United States Patent
Scirica et al.

(10) Patent No.: US 10,709,445 B2
(45) Date of Patent: *Jul. 14, 2020

(54) LOADING UNIT INCLUDING SHIPPING ASSEMBLY

(71) Applicant: Covidien LP, Mansfield, MA (US)

(72) Inventors: Paul Scirica, Huntington, CT (US); Justin Williams, Southbury, CT (US); Patrick Mozdzierz, Glastonbury, CT (US); Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 311 days.

This patent is subject to a terminal disclaimer.

(21) Appl. No.: 15/672,706

(22) Filed: Aug. 9, 2017

(65) Prior Publication Data

US 2017/0333036 A1 Nov. 23, 2017

Related U.S. Application Data

(63) Continuation of application No. 14/321,336, filed on Jul. 1, 2014, now Pat. No. 9,730,694.

(51) Int. Cl.
*A61B 17/068* (2006.01)
*A61B 1/00* (2006.01)
(Continued)

(52) U.S. Cl.
CPC ........ *A61B 17/068* (2013.01); *A61B 1/00089* (2013.01); *A61B 1/00137* (2013.01);
(Continued)

(58) Field of Classification Search
CPC ... A61B 17/068; A61B 50/30; A61B 1/00137; A61B 1/32; A61B 17/0682;
(Continued)

(56) References Cited

U.S. PATENT DOCUMENTS 3,315,863 A * 4/1967 O'Dea ................ A61B 17/072
227/19
4,505,272 A 3/1985 Utyamyshev et al.
(Continued)

FOREIGN PATENT DOCUMENTS

CN 102755179 A 10/2012
EP 2462875 A2 6/2012
(Continued)

OTHER PUBLICATIONS

Japanese Office Action dated Mar. 11, 2019, issued in JP Appln. No. 2015131192 (translation not provided).
(Continued)

*Primary Examiner* — Nathaniel C Chukwurah
*Assistant Examiner* — Lucas E. A. Palmer
(74) *Attorney, Agent, or Firm* — Carter, DeLuca & Farrell LLP

(57) ABSTRACT

A loading unit including a shipping assembly is provided. The shipping assembly is operably received adjacent the cartridge assembly to retain staples with the cartridge assembly. The shipping assembly includes a shipping member selectively secured to loading unit and a locking member slidably disposed within the shipping member. The locking member is movable between a proximal position wherein the shipping member is secured to the housing and a distal position wherein the shipping member is removable from the housing.

19 Claims, 19 Drawing Sheets

(51) Int. Cl.
*A61B 1/32* (2006.01)
*A61B 17/072* (2006.01)
*A61B 17/115* (2006.01)
*A61B 50/30* (2016.01)
*A61B 17/00* (2006.01)
*A61B 90/00* (2016.01)

(52) U.S. Cl.
CPC ............ *A61B 1/32* (2013.01); *A61B 17/0682* (2013.01); *A61B 17/072* (2013.01); *A61B 17/1155* (2013.01); *A61B 50/30* (2016.02); *A61B 2017/00473* (2013.01); *A61B 2017/07271* (2013.01); *A61B 2017/07285* (2013.01); *A61B 2090/038* (2016.02); *A61B 2090/0801* (2016.02)

(58) Field of Classification Search
CPC .............. A61B 17/072; A61B 17/1155; A61B 2090/038; A61B 2090/0801; A61B 2017/00473; A61B 2017/07271; A61B 2017/07285
USPC .................................. 206/234, 339–341, 349
See application file for complete search history.

(56) References Cited

U.S. PATENT DOCUMENTS

| | | | |
|---|---|---|---|
| 5,250,058 A | 10/1993 | Miller et al. | |
| 5,292,053 A * | 3/1994 | Bilotti | A61B 17/115 227/179.1 |
| 5,366,133 A * | 11/1994 | Geiste | A61B 17/07207 227/175.1 |
| 5,533,661 A * | 7/1996 | Main | A61B 17/115 227/176.1 |
| 5,669,918 A | 9/1997 | Balazs et al. | |
| 5,836,503 A | 11/1998 | Ehrenfels et al. | |
| 5,868,760 A * | 2/1999 | McGuckin, Jr. | A61B 17/00234 227/179.1 |
| 5,988,479 A * | 11/1999 | Palmer | A61B 17/07207 227/175.4 |
| 6,050,472 A | 4/2000 | Shibata | |
| 6,119,913 A * | 9/2000 | Adams | A61B 17/115 227/176.1 |
| 6,126,058 A * | 10/2000 | Adams | A61B 17/07207 227/179.1 |
| 6,398,795 B1 * | 6/2002 | McAlister | A61B 17/068 227/179.1 |
| 6,439,446 B1 * | 8/2002 | Perry | A61B 17/072 227/175.2 |
| 6,695,198 B2 * | 2/2004 | Adams | A61B 17/072 227/156 |
| 6,945,444 B2 * | 9/2005 | Gresham | A61B 17/115 227/175.1 |
| 6,957,758 B2 * | 10/2005 | Aranyi | A61B 17/072 227/176.1 |
| 6,959,851 B2 * | 11/2005 | Heinrich | A61B 17/115 227/152 |
| D532,108 S * | 11/2006 | Milliman | D24/145 |
| 7,147,140 B2 * | 12/2006 | Wukusick | A61B 17/072 227/182.1 |
| 7,168,604 B2 * | 1/2007 | Milliman | A61B 17/1114 227/175.1 |
| 7,182,239 B1 | 2/2007 | Myers | |
| 7,210,609 B2 * | 5/2007 | Leiboff | A61B 17/115 227/180.1 |
| 7,293,685 B2 * | 11/2007 | Ehrenfels | A61B 17/07207 227/175.1 |
| 7,303,106 B2 * | 12/2007 | Milliman | A61B 17/115 227/175.1 |
| 7,326,232 B2 * | 2/2008 | Viola | A61B 17/07207 227/175.1 |
| 7,364,060 B2 * | 4/2008 | Milliman | A61B 17/068 227/175.1 |
| 7,494,038 B2 * | 2/2009 | Milliman | A61B 17/115 227/176.1 |
| 7,942,302 B2 * | 5/2011 | Roby | A61B 17/115 227/175.1 |
| 7,975,895 B2 * | 7/2011 | Milliman | A61B 17/1155 227/175.1 |
| 8,006,701 B2 | 8/2011 | Bilotti et al. | |
| 8,011,554 B2 * | 9/2011 | Milliman | A61B 17/115 227/175.1 |
| 8,075,577 B2 * | 12/2011 | Deem | A61B 17/064 606/153 |
| 8,118,206 B2 | 2/2012 | Zand et al. | |
| 8,146,790 B2 * | 4/2012 | Milliman | A61B 17/115 227/175.2 |
| 8,181,838 B2 * | 5/2012 | Milliman | A61B 1/31 227/175.1 |
| 8,231,042 B2 * | 7/2012 | Hessler | A61B 17/1114 227/175.1 |
| 8,267,301 B2 * | 9/2012 | Milliman | A61B 17/115 227/176.1 |
| 8,272,555 B2 * | 9/2012 | Rebuffat | A61B 17/115 227/179.1 |
| 8,281,974 B2 * | 10/2012 | Hessler | A61B 17/115 227/175.1 |
| 8,322,590 B2 * | 12/2012 | Patel | A61B 17/115 227/176.1 |
| 8,397,972 B2 * | 3/2013 | Kostrzewski | A61B 17/07207 227/175.2 |
| 8,430,292 B2 * | 4/2013 | Patel | A61B 17/115 227/181.1 |
| 8,453,913 B2 * | 6/2013 | Milliman | A61B 17/07207 227/179.1 |
| 8,540,132 B2 * | 9/2013 | Marczyk | A61B 17/115 227/175.1 |
| 8,579,937 B2 * | 11/2013 | Gresham | A61B 17/068 606/219 |
| 8,590,764 B2 * | 11/2013 | Hartwick | A61B 17/00234 227/179.1 |
| 8,678,264 B2 * | 3/2014 | Racenet | A61B 17/115 227/175.1 |
| 8,708,212 B2 * | 4/2014 | Williams | A61B 17/1155 227/175.1 |
| 8,714,352 B2 * | 5/2014 | Farascioni | A61B 17/072 206/340 |
| 8,794,497 B2 * | 8/2014 | Zingman | A61B 17/072 227/175.2 |
| 8,925,788 B2 * | 1/2015 | Hess | A61B 17/32 227/180.1 |
| 8,931,682 B2 * | 1/2015 | Timm | A61B 17/072 227/178.1 |
| 8,973,804 B2 * | 3/2015 | Hess | A61B 17/0644 227/175.1 |
| 8,978,954 B2 * | 3/2015 | Shelton, IV | A61B 17/00491 227/175.1 |
| 8,991,677 B2 * | 3/2015 | Moore | A61B 17/072 227/175.2 |
| 9,010,605 B2 * | 4/2015 | Olson | A61B 17/1155 227/175.1 |
| 9,016,547 B2 * | 4/2015 | Mozdzierz | A61B 17/1155 227/179.1 |
| 9,022,274 B2 * | 5/2015 | Penna | A61B 17/115 227/175.1 |
| 9,028,494 B2 * | 5/2015 | Shelton, IV | A61B 34/30 606/51 |
| 9,038,882 B2 * | 5/2015 | Racenet | A61B 17/072 227/180.1 |
| 9,044,230 B2 * | 6/2015 | Morgan | A61B 17/07207 |
| 9,050,084 B2 * | 6/2015 | Schmid | A61B 17/07207 |
| 9,055,941 B2 * | 6/2015 | Schmid | A61B 17/00491 |
| 9,060,770 B2 * | 6/2015 | Shelton, IV | A61B 17/07207 |
| 9,072,515 B2 * | 7/2015 | Hall | A61B 17/07207 |
| 9,072,535 B2 * | 7/2015 | Shelton, IV | A61B 17/07207 |
| 9,072,536 B2 * | 7/2015 | Shelton, IV | A61B 34/30 |
| 9,078,653 B2 * | 7/2015 | Leimbach | A61B 17/07207 |

(56) References Cited

U.S. PATENT DOCUMENTS

| | | | |
|---|---|---|---|
| 9,101,358 B2* | 8/2015 | Kerr | A61B 17/07207 |
| 9,101,385 B2* | 8/2015 | Shelton, IV | A61B 18/1445 |
| 9,107,662 B2* | 8/2015 | Kostrzewski | A61B 17/068 |
| 9,113,874 B2* | 8/2015 | Shelton, IV | A61B 17/07207 |
| 9,119,657 B2* | 9/2015 | Shelton, IV | A61B 17/29 |
| 9,125,662 B2* | 9/2015 | Shelton, IV | A61B 18/1445 |
| 9,131,940 B2* | 9/2015 | Huitema | A61B 17/07207 |
| 9,138,225 B2* | 9/2015 | Huang | A61B 17/068 |
| 9,186,141 B2* | 11/2015 | Williams | A61B 17/072 |
| 9,198,662 B2* | 12/2015 | Barton | A61B 17/07207 |
| 9,204,878 B2* | 12/2015 | Hall | A61B 17/07207 |
| 9,204,879 B2* | 12/2015 | Shelton, IV | A61B 17/07207 |
| 9,204,880 B2* | 12/2015 | Baxter, III | A61B 17/07292 |
| 9,211,120 B2* | 12/2015 | Scheib | A61B 17/068 |
| 9,220,500 B2* | 12/2015 | Swayze | A61B 17/07292 |
| 9,220,501 B2* | 12/2015 | Baxter, III | A61B 17/0643 |
| 9,226,751 B2* | 1/2016 | Shelton, IV | A61B 17/07207 |
| 9,232,941 B2* | 1/2016 | Mandakolathur Vasudevan | A61B 17/00491 |
| 9,265,503 B2* | 2/2016 | Vestweber | A61B 17/11 |
| 9,272,406 B2* | 3/2016 | Aronhalt | A61B 17/0682 |
| 9,282,974 B2* | 3/2016 | Shelton, IV | A61B 17/1285 |
| 9,283,054 B2* | 3/2016 | Morgan | A61B 34/74 |
| 9,289,210 B2* | 3/2016 | Baxter, III | A61B 17/07207 |
| 9,289,212 B2* | 3/2016 | Shelton, IV | A61B 1/00027 |
| 9,289,256 B2* | 3/2016 | Shelton, IV | A61B 18/1442 |
| 9,301,752 B2* | 4/2016 | Mandakolathur Vasudevan | A61B 17/00491 |
| 9,301,759 B2* | 4/2016 | Spivey | A61B 17/07207 |
| 9,307,986 B2* | 4/2016 | Hall | A61B 17/07207 |
| 9,307,987 B2* | 4/2016 | Swensgard | A61B 17/07207 |
| 9,307,988 B2* | 4/2016 | Shelton, IV | A61B 17/064 |
| 9,307,989 B2* | 4/2016 | Shelton, IV | A61B 17/07207 |
| 9,314,246 B2* | 4/2016 | Shelton, IV | A61B 17/00491 |
| 9,314,247 B2* | 4/2016 | Shelton, IV | A61B 17/07292 |
| 9,320,521 B2* | 4/2016 | Shelton, IV | A61B 17/0682 |
| 9,320,523 B2* | 4/2016 | Shelton, IV | A61B 17/07207 |
| 9,326,768 B2* | 5/2016 | Shelton, IV | A61B 17/07207 |
| 9,326,769 B2* | 5/2016 | Shelton, IV | A61B 17/072 |
| 9,332,974 B2* | 5/2016 | Henderson | A61B 17/00491 |
| 9,332,984 B2* | 5/2016 | Weaner | A61B 17/07207 |
| 9,332,987 B2* | 5/2016 | Leimbach | A61B 34/30 |
| 9,345,481 B2* | 5/2016 | Hall | A61B 17/068 |
| 9,351,724 B2* | 5/2016 | Penna | A61B 17/068 |
| 9,351,726 B2* | 5/2016 | Leimbach | A61B 17/068 |
| 9,351,727 B2* | 5/2016 | Leimbach | A61B 17/068 |
| 9,351,734 B2* | 5/2016 | Prior | A61B 17/115 |
| 9,358,005 B2* | 6/2016 | Shelton, IV | A61B 17/068 |
| 9,364,230 B2* | 6/2016 | Shelton, IV | A61B 17/07207 |
| 9,364,233 B2* | 6/2016 | Alexander, III | A61B 17/00491 |
| 9,370,358 B2* | 6/2016 | Shelton, IV | A61B 17/07207 |
| 9,370,364 B2* | 6/2016 | Smith | A61B 17/07207 |
| 9,386,984 B2* | 7/2016 | Aronhalt | A61B 17/072 |
| 9,393,015 B2* | 7/2016 | Laurent | A61B 90/30 |
| 9,408,604 B2* | 8/2016 | Shelton, IV | A61B 17/072 |
| 9,408,606 B2* | 8/2016 | Shelton, IV | A61B 17/07207 |
| 9,486,214 B2* | 11/2016 | Shelton, IV | A61B 17/07207 |
| 9,492,167 B2* | 11/2016 | Shelton, IV | A61B 17/068 |
| 9,517,070 B2* | 12/2016 | Mulreed | A61B 17/115 |
| 9,522,029 B2* | 12/2016 | Yates | A61B 17/07207 |
| 9,532,780 B2* | 1/2017 | Williams | A61B 17/115 |
| 9,549,735 B2* | 1/2017 | Shelton, IV | A61B 17/0644 |
| 9,554,802 B2* | 1/2017 | Williams | A61B 17/1155 |
| 9,561,038 B2* | 2/2017 | Shelton, IV | A61B 17/1285 |
| 9,572,572 B2* | 2/2017 | Williams | A61B 17/068 |
| 9,572,577 B2* | 2/2017 | Lloyd | A61B 17/07292 |
| 9,574,644 B2* | 2/2017 | Parihar | F16H 19/02 |
| 9,585,657 B2* | 3/2017 | Shelton, IV | A61B 17/07207 |
| 9,585,660 B2* | 3/2017 | Laurent | A61B 17/072 |
| 9,585,662 B2* | 3/2017 | Shelton, IV | A61B 17/0644 |
| 9,592,052 B2* | 3/2017 | Shelton, IV | A61B 17/07207 |
| 9,592,053 B2* | 3/2017 | Shelton, IV | A61B 17/064 |
| 9,592,056 B2* | 3/2017 | Mozdzierz | A61B 17/1155 |
| 9,597,083 B2* | 3/2017 | Penna | A61B 17/068 |
| 9,603,598 B2* | 3/2017 | Shelton, IV | A61B 17/105 |
| 9,603,991 B2* | 3/2017 | Shelton, IV | A61B 17/00491 |
| 9,615,826 B2* | 4/2017 | Shelton, IV | A61B 17/068 |
| 9,629,629 B2* | 4/2017 | Leimbach | A61B 17/07207 |
| 9,629,814 B2* | 4/2017 | Widenhouse | A61B 17/07292 |
| 9,642,620 B2* | 5/2017 | Baxter, III | A61B 17/072 |
| 9,649,110 B2* | 5/2017 | Parihar | A61B 17/068 |
| 9,655,614 B2* | 5/2017 | Swensgard | A61B 17/068 |
| 9,668,740 B2* | 6/2017 | Williams | A61B 17/1155 |
| 9,675,359 B2* | 6/2017 | Williams | A61B 17/1155 |
| 9,681,870 B2* | 6/2017 | Baxter, III | A61B 17/07207 |
| 9,687,230 B2* | 6/2017 | Leimbach | A61B 17/064 |
| 9,687,231 B2* | 6/2017 | Baxter, III | A61B 17/0644 |
| 9,687,236 B2* | 6/2017 | Leimbach | A61B 17/07207 |
| 9,690,362 B2* | 6/2017 | Leimbach | A61B 17/068 |
| 9,693,773 B2* | 7/2017 | Williams | A61B 17/1114 |
| 9,693,777 B2* | 7/2017 | Schellin | B29C 55/00 |
| 9,724,092 B2* | 8/2017 | Baxter, III | A61B 17/07207 |
| 9,724,094 B2* | 8/2017 | Baber | A61B 90/92 |
| 9,724,098 B2* | 8/2017 | Baxter, III | A61B 17/0644 |
| 9,730,694 B2 | 8/2017 | Scirica et al. | |
| 9,737,301 B2* | 8/2017 | Baber | H02H 3/06 |
| 9,743,928 B2* | 8/2017 | Shelton, IV | A61B 17/07207 |
| 9,743,929 B2* | 8/2017 | Leimbach | B25F 3/00 |
| 9,750,503 B2* | 9/2017 | Milliman | A61B 90/98 |
| 9,757,123 B2* | 9/2017 | Giordano | A61B 50/30 |
| 9,757,128 B2* | 9/2017 | Baber | A61B 17/07207 |
| 9,757,133 B2* | 9/2017 | Latimer | A61B 90/30 |
| 9,763,662 B2* | 9/2017 | Shelton, IV | A61B 17/07207 |
| 9,770,245 B2* | 9/2017 | Swayze | A61B 17/068 |
| 9,788,836 B2* | 10/2017 | Overmyer | A61B 17/105 |
| 9,795,382 B2* | 10/2017 | Shelton, IV | A61B 17/0682 |
| 9,795,384 B2* | 10/2017 | Weaner | A61B 17/07207 |
| 9,801,627 B2* | 10/2017 | Harris | A61B 17/07207 |
| 9,801,628 B2* | 10/2017 | Harris | A61B 17/072 |
| 9,808,244 B2* | 11/2017 | Leimbach | A61B 17/07207 |
| 9,808,246 B2* | 11/2017 | Shelton, IV | A61B 17/068 |
| 9,814,462 B2* | 11/2017 | Woodard, Jr. | A61B 17/072 |
| 9,820,738 B2* | 11/2017 | Lytle, IV | A61B 90/98 |
| 9,826,978 B2* | 11/2017 | Shelton, IV | A61B 17/068 |
| 9,833,241 B2* | 12/2017 | Huitema | G06F 11/1425 |
| 9,839,420 B2* | 12/2017 | Shelton, IV | H05K 999/99 |
| 9,839,427 B2* | 12/2017 | Swayze | A61B 17/072 |
| 9,839,428 B2* | 12/2017 | Baxter, III | A61B 17/07207 |
| 9,839,429 B2* | 12/2017 | Weisenburgh, II | A61B 17/07207 |
| 9,844,374 B2* | 12/2017 | Lytle, IV | A61B 17/07207 |
| 9,844,375 B2* | 12/2017 | Overmyer | A61B 17/07207 |
| 9,844,376 B2* | 12/2017 | Baxter, III | A61B 17/07207 |
| 9,855,045 B2* | 1/2018 | Williams | A61B 17/1155 |
| 9,861,359 B2* | 1/2018 | Shelton, IV | A61B 17/068 |
| 9,861,367 B2* | 1/2018 | Williams | A61B 17/068 |
| 9,867,619 B2* | 1/2018 | Williams | A61B 17/064 |
| 9,888,919 B2* | 2/2018 | Leimbach | A61B 17/07207 |
| 9,895,147 B2* | 2/2018 | Shelton, IV | A61B 17/07207 |
| 9,895,148 B2* | 2/2018 | Shelton, IV | A61B 17/068 |
| 9,901,342 B2* | 2/2018 | Shelton, IV | A61B 17/072 |
| 9,913,642 B2* | 3/2018 | Leimbach | A61B 17/072 |
| 9,913,643 B2* | 3/2018 | Penna | A61B 17/1155 |
| 9,924,944 B2* | 3/2018 | Shelton, IV | A61B 17/07207 |
| 9,924,961 B2* | 3/2018 | Shelton, IV | A61B 17/295 |
| 9,931,118 B2* | 4/2018 | Shelton, IV | A61B 17/2909 |
| 9,943,309 B2* | 4/2018 | Shelton, IV | A61B 17/0644 |
| 9,974,536 B2* | 5/2018 | Sgroi, Jr. | A61B 17/0469 |
| 9,980,730 B2* | 5/2018 | Sgroi | A61B 17/068 |
| 9,987,000 B2* | 6/2018 | Shelton, IV | A61B 17/07207 |
| 9,987,001 B2* | 6/2018 | Williams | A61B 17/068 |
| 9,993,248 B2* | 6/2018 | Shelton, IV | A61B 17/072 |
| 9,993,258 B2* | 6/2018 | Shelton, IV | A61B 17/072 |
| 10,004,498 B2* | 6/2018 | Morgan | A61B 17/072 |
| D822,206 S * | 7/2018 | Shelton, IV | D24/145 |
| 10,022,126 B2* | 7/2018 | Sgroi, Jr. | A61B 17/1155 |
| 10,028,744 B2* | 7/2018 | Shelton, IV | A61B 17/115 |
| D826,405 S * | 8/2018 | Shelton, IV | D24/145 |
| 10,039,529 B2* | 8/2018 | Kerr | A61B 17/07207 |
| 10,039,549 B2* | 8/2018 | Williams | A61B 17/105 |
| 10,045,776 B2* | 8/2018 | Shelton, IV | A61B 17/068 |
| 10,045,781 B2* | 8/2018 | Cropper | A61B 17/07207 |
| 10,052,044 B2* | 8/2018 | Shelton, IV | A61B 18/1445 |

(56) References Cited

U.S. PATENT DOCUMENTS

| | | | |
|---|---|---|---|
| 10,052,102 B2 * | 8/2018 | Baxter, III | A61B 17/105 |
| 10,058,963 B2 * | 8/2018 | Shelton, IV | A61B 34/30 |
| 10,076,325 B2 * | 9/2018 | Huang | A61B 17/07207 |
| 10,076,326 B2 * | 9/2018 | Yates | A61B 17/00 |
| 10,085,744 B2 * | 10/2018 | Williams | A61B 17/068 |
| 10,085,748 B2 * | 10/2018 | Morgan | A61B 17/072 |
| 10,085,751 B2 * | 10/2018 | Overmyer | G01R 19/00 |
| 10,085,756 B2 * | 10/2018 | Williams | A61B 17/00234 |
| 10,105,139 B2 * | 10/2018 | Yates | A61B 17/072 |
| 10,111,668 B2 * | 10/2018 | Penna | A61B 17/072 |
| 10,111,684 B2 * | 10/2018 | Williams | A61B 17/115 |
| 10,117,649 B2 * | 11/2018 | Baxter, III | A61B 17/072 |
| 10,117,655 B2 * | 11/2018 | Scirica | A61B 17/105 |
| 10,117,656 B2 * | 11/2018 | Sgroi, Jr. | A61B 17/1155 |
| 10,117,675 B2 * | 11/2018 | Cabrera | A61B 17/068 |
| 10,130,359 B2 * | 11/2018 | Hess | F16B 15/00 |
| 10,130,363 B2 * | 11/2018 | Huitema | A61B 17/07207 |
| 10,135,242 B2 * | 11/2018 | Baber | A61B 17/0644 |
| 10,172,619 B2 * | 1/2019 | Harris | A61B 17/105 |
| 10,172,620 B2 * | 1/2019 | Harris | A61B 17/068 |
| 10,178,994 B2 * | 1/2019 | Lee | A61B 17/1155 |
| 10,180,463 B2 * | 1/2019 | Beckman | G01R 31/36 |
| 10,188,385 B2 * | 1/2019 | Kerr | A61B 17/07207 |
| 10,206,676 B2 * | 2/2019 | Shelton, IV | A61B 17/105 |
| 10,211,586 B2 * | 2/2019 | Adams | H01R 39/24 |
| 10,213,201 B2 * | 2/2019 | Shelton, IV | A61B 17/07292 |
| 10,213,205 B2 * | 2/2019 | Williams | A61B 17/115 |
| 10,226,249 B2 * | 3/2019 | Jaworek | A61B 17/07207 |
| 10,238,386 B2 * | 3/2019 | Overmyer | A61B 17/068 |
| 10,238,390 B2 * | 3/2019 | Harris | A61B 17/068 |
| 10,245,030 B2 * | 4/2019 | Hunter | A61B 17/32 |
| 10,245,033 B2 * | 4/2019 | Overmyer | A61B 17/072 |
| 10,258,331 B2 * | 4/2019 | Shelton, IV | A61B 17/068 |
| 10,258,333 B2 * | 4/2019 | Shelton, IV | A61B 17/07207 |
| 10,258,418 B2 * | 4/2019 | Shelton, IV | G05B 19/4015 |
| 10,265,068 B2 * | 4/2019 | Harris | A61B 17/068 |
| 10,271,843 B2 * | 4/2019 | Shi | A61B 17/1155 |
| 10,271,849 B2 * | 4/2019 | Vendely | A61B 17/068 |
| 10,271,851 B2 * | 4/2019 | Shelton, IV | A61B 17/1155 |
| D847,989 S * | 5/2019 | Shelton, IV | D24/145 |
| 10,278,780 B2 * | 5/2019 | Shelton, IV | A61B 17/00234 |
| 10,285,699 B2 * | 5/2019 | Vendely | A61B 17/068 |
| 10,285,705 B2 * | 5/2019 | Shelton, IV | A61B 17/0644 |
| 10,292,704 B2 * | 5/2019 | Harris | A61B 17/072 |
| 10,299,878 B2 * | 5/2019 | Shelton, IV | A61B 90/06 |
| D850,617 S * | 6/2019 | Shelton, IV | D24/145 |
| D851,762 S * | 6/2019 | Shelton, IV | D24/145 |
| 10,307,159 B2 * | 6/2019 | Harris | A61B 17/07207 |
| 10,307,160 B2 * | 6/2019 | Vendely | A61B 17/072 |
| 10,307,170 B2 * | 6/2019 | Parfett | A61B 17/1626 |
| 10,327,767 B2 * | 6/2019 | Shelton, IV | A61B 17/0686 |
| 10,327,769 B2 * | 6/2019 | Overmyer | A61B 17/07207 |
| D854,151 S * | 7/2019 | Shelton, IV | D24/145 |
| 10,335,145 B2 * | 7/2019 | Harris | A61B 17/07207 |
| 10,342,534 B2 * | 7/2019 | Williams | A61B 17/068 |
| 10,342,543 B2 * | 7/2019 | Shelton, IV | A61B 17/068 |
| 10,357,247 B2 * | 7/2019 | Shelton, IV | A61B 17/068 |
| 10,363,036 B2 * | 7/2019 | Yates | H02P 7/00 |
| 10,363,037 B2 * | 7/2019 | Aronhalt | A61B 17/068 |
| 10,368,863 B2 * | 8/2019 | Timm | A61B 17/068 |
| 10,368,864 B2 * | 8/2019 | Harris | A61B 17/0686 |
| 10,368,865 B2 * | 8/2019 | Harris | A61B 17/072 |
| 10,368,867 B2 * | 8/2019 | Harris | A61B 17/07207 |
| 2002/0020732 A1 | 2/2002 | Adams et al. | |
| 2005/0107811 A1 | 5/2005 | Starksen et al. | |
| 2008/0172087 A1 | 7/2008 | Fuchs et al. | |
| 2009/0012556 A1 | 1/2009 | Boudreaux et al. | |
| 2009/0082777 A1 | 3/2009 | Milliman et al. | |
| 2011/0101066 A1 | 5/2011 | Farascioni et al. | |
| 2011/0114699 A1 | 5/2011 | Baxter, III et al. | |
| 2012/0132663 A1 | 5/2012 | Kasvikis et al. | |
| 2012/0145714 A1 | 6/2012 | Farascioni et al. | |
| 2012/0234894 A1 | 9/2012 | Kostrzewski | |
| 2013/0098968 A1 | 4/2013 | Aranyi | |
| 2013/0146643 A1 | 6/2013 | Schmid et al. | |
| 2014/0100425 A1 | 4/2014 | Metras | |
| 2014/0224686 A1 | 8/2014 | Aronhalt et al. | |
| 2014/0291377 A1 | 10/2014 | Sarin | |
| 2015/0108198 A1 | 4/2015 | Estrella | |
| 2015/0173757 A1 | 6/2015 | Williams et al. | |
| 2015/0190133 A1 | 7/2015 | Penna et al. | |
| 2016/0095756 A1 | 4/2016 | Zurovoik | |
| 2016/0270783 A1 | 9/2016 | Yigit et al. | |

FOREIGN PATENT DOCUMENTS

| | | |
|---|---|---|
| EP | 2730237 A1 | 5/2014 |
| EP | 2752162 A1 | 7/2014 |
| JP | 2009136670 A | 6/2009 |
| JP | 2014094282 A | 5/2014 |
| JP | 2014094283 A | 5/2014 |
| WO | 2007147439 A1 | 12/2007 |
| WO | 2013026402 A1 | 2/2013 |

OTHER PUBLICATIONS

EP Office Action dated Jul. 27, 2017, issued in EP Application No. 15 174 462.
Chinese Office Action dated Sep. 27, 2018 issued in Chinese Application No. 20150379396.
Extended European Seach Report issued in corresponding EP 15174462 dated Nov. 9, 2015.
EP Office Action dated Feb. 23, 2017, issued in EP Appln. No. 15174462.
Australian Office Action dated Feb. 1, 2019, issued in AU Appln. No. 2015202932.

* cited by examiner

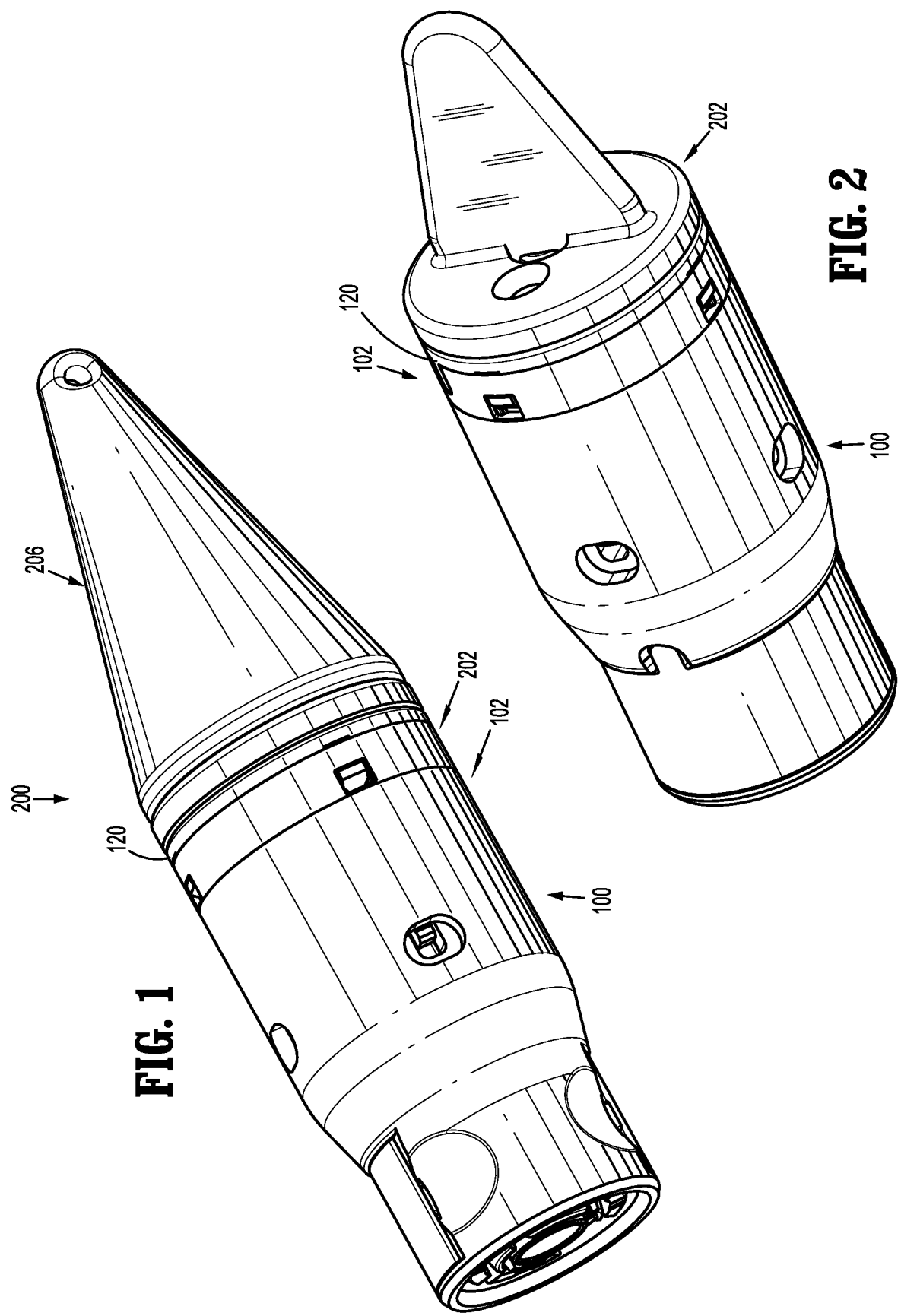

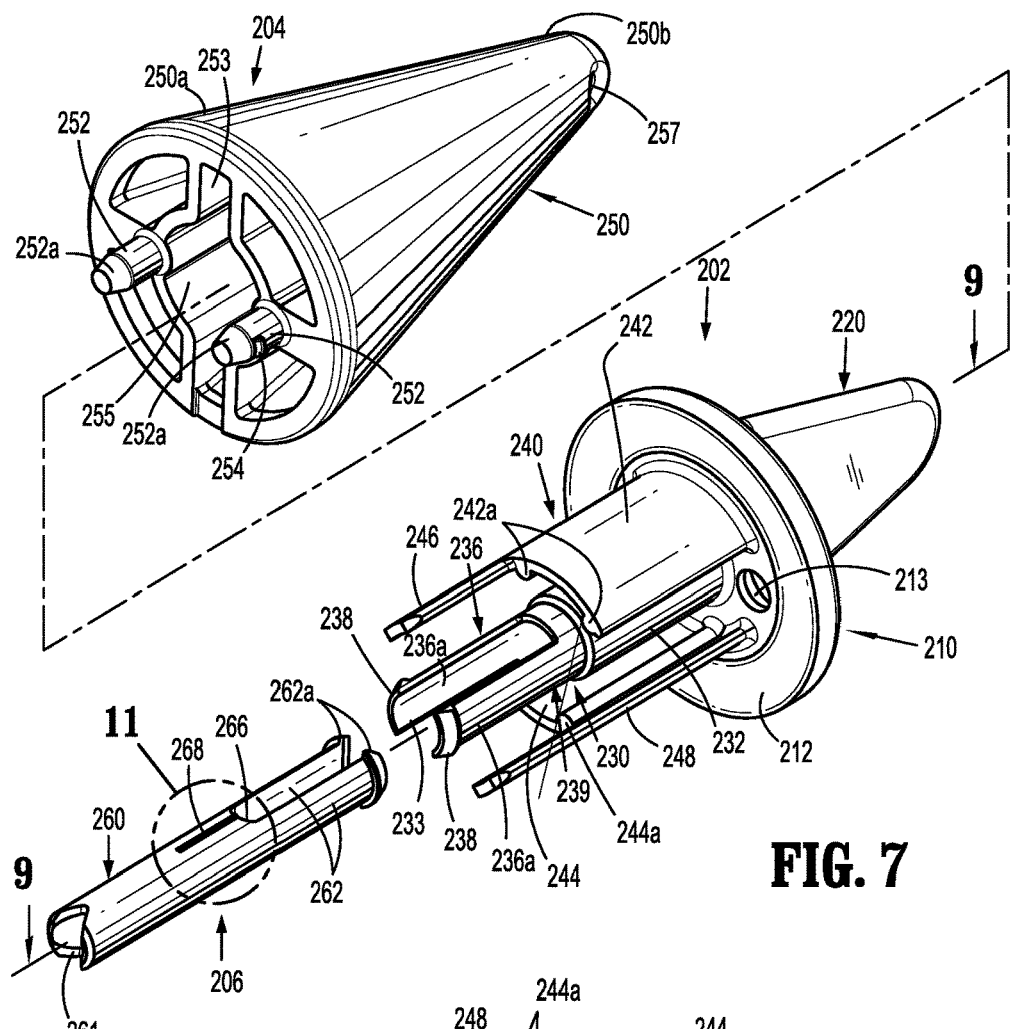
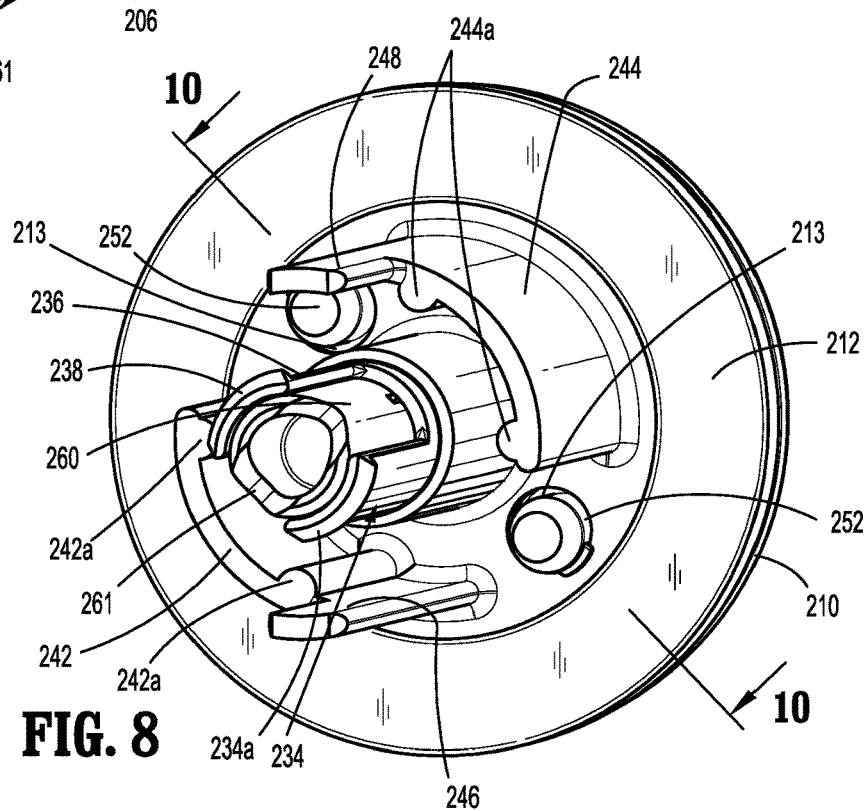
FIG. 7
FIG. 8

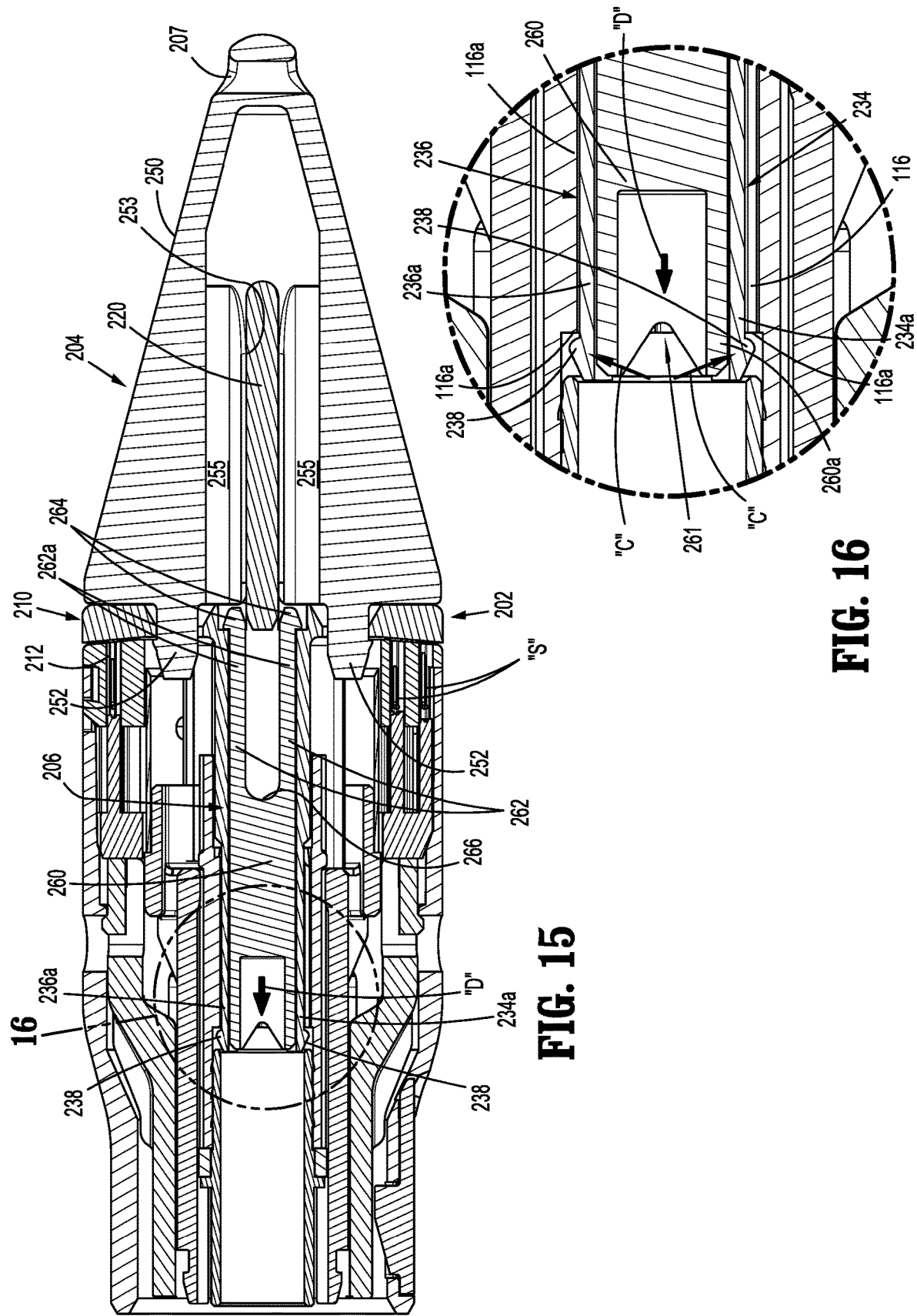

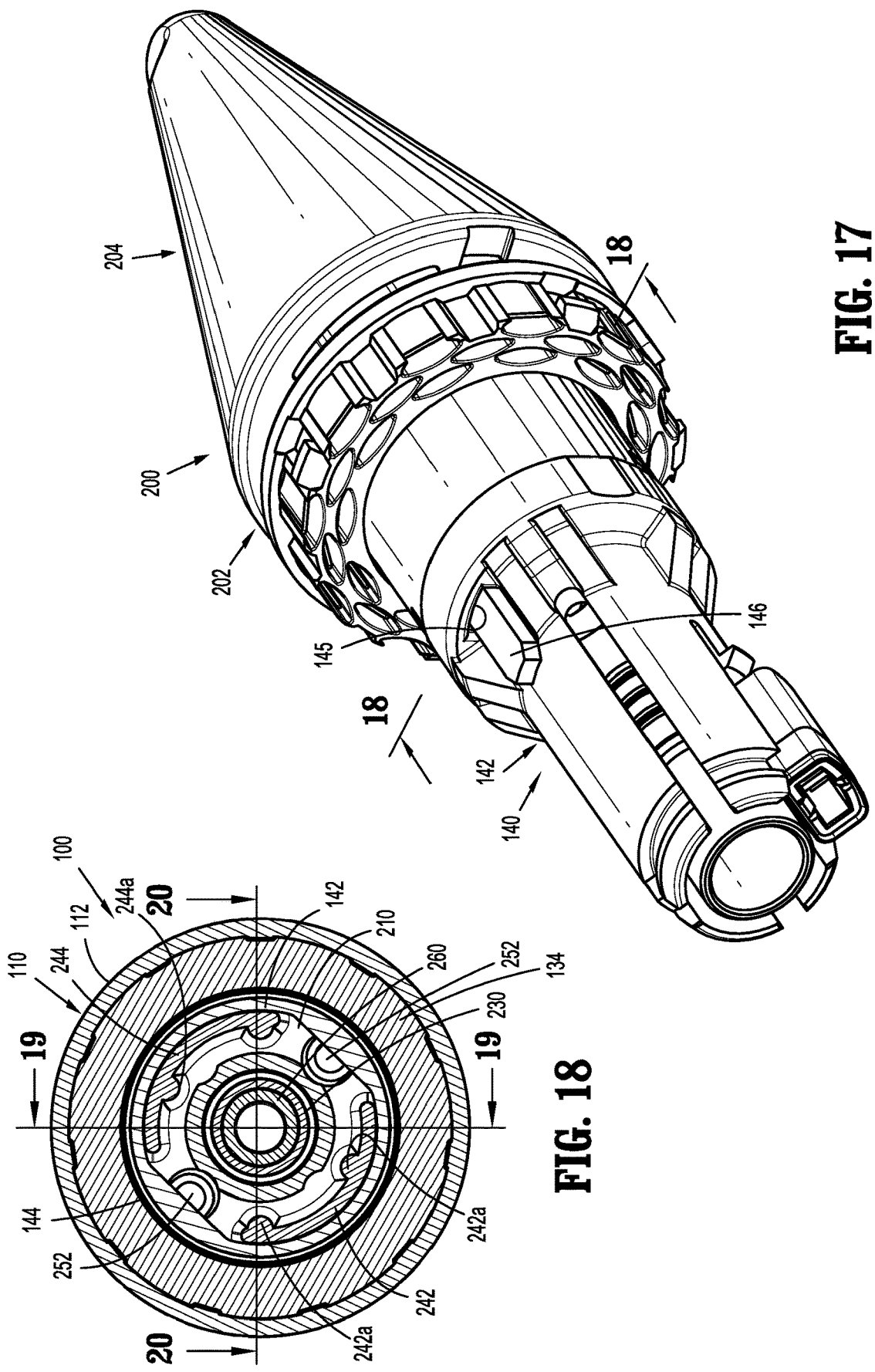

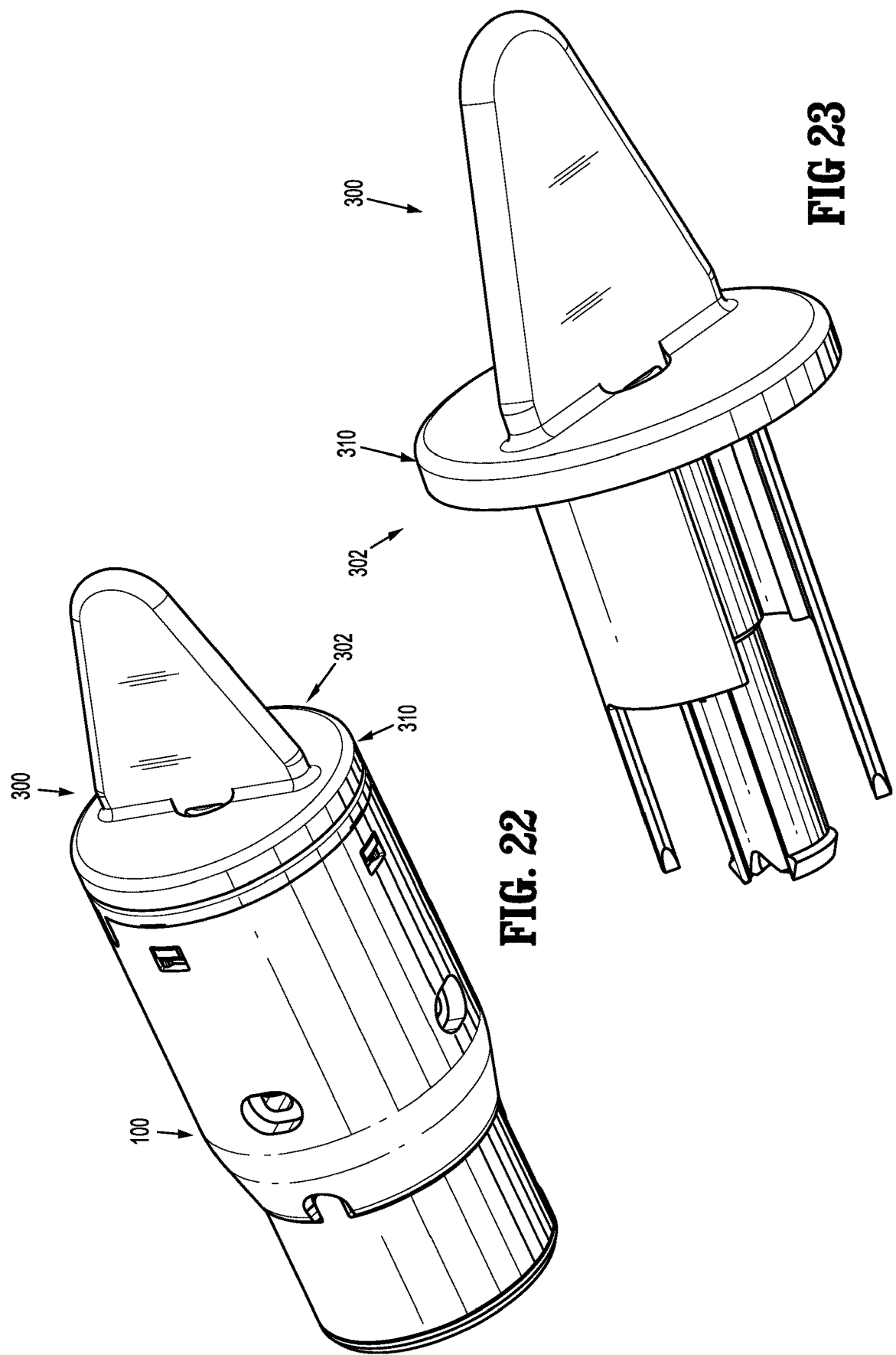

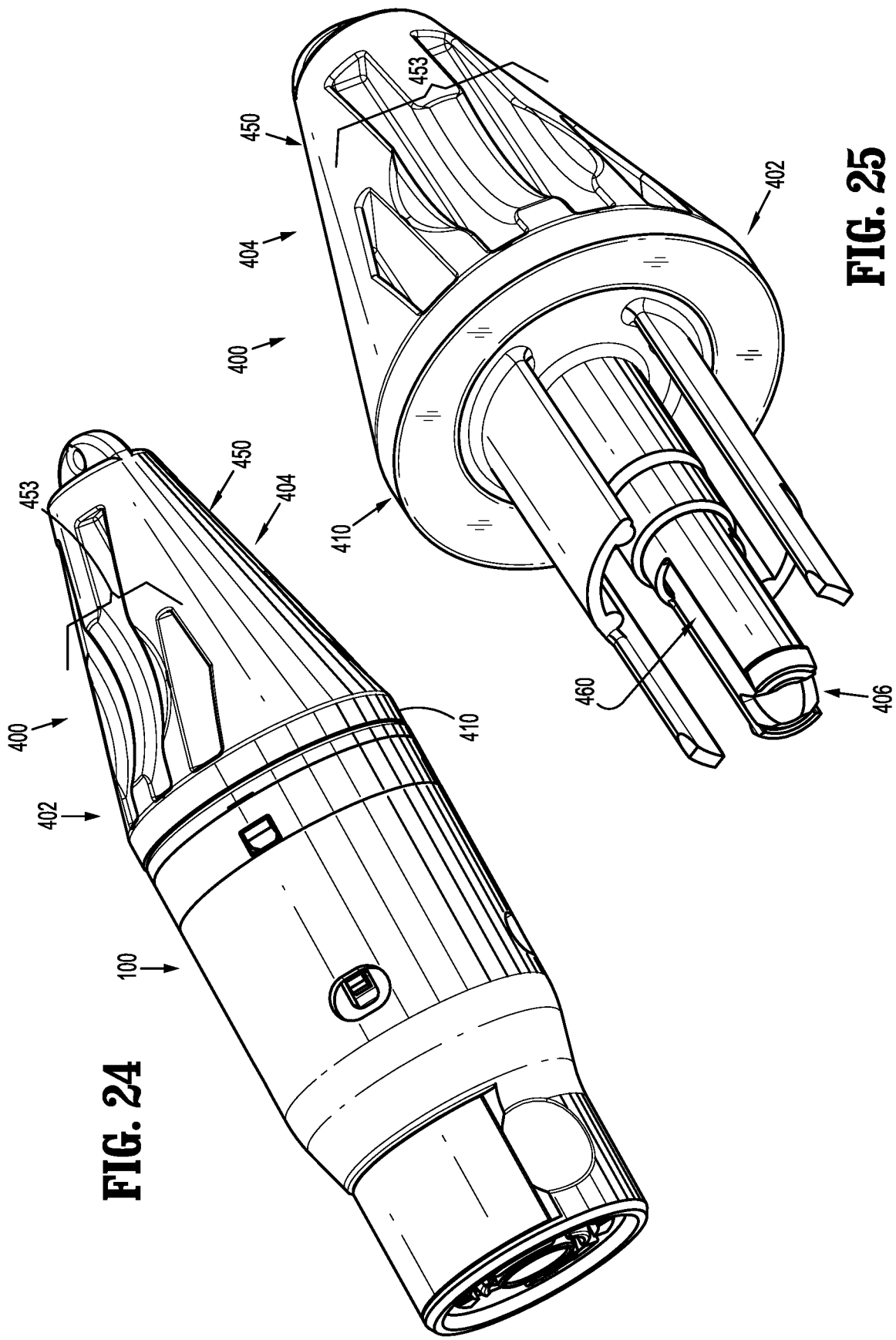

LOADING UNIT INCLUDING SHIPPING ASSEMBLY

CROSS-REFERENCE TO RELATED APPLICATIONS

The present application is a Continuation Application which claims that benefit of and priority to U.S. patent application Ser. No. 14/321,336, filed on Jul. 1, 2014, the entire content of which is incorporated herein by reference.

BACKGROUND

Technical Field

The present disclosure relates to surgical stapling devices including replaceable loading units. More particularly, the present disclosure relates to replaceable loading units including a shipping assembly.

Background of Related Art

Surgical devices for applying staples, clips, or other fasteners to tissue are well known. Endoscopic surgical devices for applying surgical fasteners include a handle assembly for actuating the device, a shaft for endoscopic access, and a tool assembly disposed at a distal end of the shaft. Certain of these devices are designed for use with a replaceable loading unit which includes the tool assembly and houses the staples or fasteners. The replaceable loading unit may include staples of various sizes and the staples may be arranged in one or more configurations. After firing the stapler with a replaceable loading unit, the user may remove the empty loading unit, select and attach to the stapler another loading unit, and fire the stapler again. This process may be performed repeatedly during a surgical procedure.

Many loading units typically include a staple cartridge, a staple pusher assembly, and, a knife assembly. In some loading units the staple pusher and knife assemblies are included in a single assembly. The staple pusher assembly and the knife assembly generally include one or more movable parts positioned to engage one or more drive members of the actuation unit. If the moving parts are not retained in a proper position prior to and during attachment of the loading unit to the actuation unit, the loading unit may not properly engage the actuation unit. Some loading units are provided with automatic locking systems which block movement of the components of the loading unit prior to attachment of the loading unit to the actuation unit and allow free movement of the movable parts of the loading unit once the loading unit has been attached to the actuation unit. However, these automatic locking systems are not configured to retain staples within the staple cartridge prior to activation of the loading unit. In addition, these locking systems are not configured to facilitate positioning of the loading unit after the loading unit has been attached to an actuation unit.

Therefore, it would be beneficial to have a shipping member configured to maintain the movable parts of the loading unit and to maintain the staples within the staple cartridge. It would further be beneficial to have a shipping member configured to facilitate positioning of the loading unit after the loading unit is attached to an actuation unit.

SUMMARY

Accordingly, a loading unit including a shipping assembly is provided. The loading unit includes a housing, a staple pusher assembly operably retained within the housing, a knife assembly operably retained within the housing, a cartridge assembly disposed on a distal end of the housing and supporting an annular array of staples. The shipping assembly is operably disposed adjacent the cartridge assembly. The shipping assembly includes a shipping member selectively secured to housing and a locking member slidably disposed within the shipping member. The locking member is movable between a proximal position wherein the shipping member is secured to the housing and a distal position wherein the shipping member is removable from the housing.

In embodiments, the shipping member includes a base portion having a staple retaining surface positioned adjacent the cartridge assembly for retaining the plurality of staples within the cartridge assembly. The shipping member may include an inner annular extension having a pair of legs each configured to selectively engage the housing for securing the shipping assembly to the housing. The shipping member may include an outer annular extension having at least one shelf and at least one leg, wherein the at least one shelf engages the knife assembly to prevent movement of the knife assembly and the at least one outer leg engages the pusher assembly to prevent movement of the pusher assembly. The shipping member may include a flange portion configured for operable engagement by a user.

In some embodiments, the shipping assembly includes an introducer member selectively securable to the flange portion. The introducer member may include a conical shape. The introducer member may include a throughbore for receiving a retrieval string. The introducer member may be configured to facilitate insertion of the loading unit through a lumen. The shipping member may include an introducer portion.

A shipping assembly for a loading unit is also provided. The shipping assembly includes a shipping member having a base portion, a flange extending distally from the base, and an inner annular extension extending proximally from the base, and a locking member slidably disposed within the annular extension and being movable between a proximal position wherein the shipping member is secured to the loading unit and a distal position wherein the shipping member is removable from the loading unit.

The shipping assembly may further include an outer annular extension having at least one shelf and at least one leg extending beyond the shelf. The base portion may include a staple retaining surface for retaining a plurality of stapes within a cartridge of the loading unit. The shipping assembly may also include an introducer member selectively securable to the flange. The introducer member may include a conical shape. In some embodiments, the introducer member includes a throughbore for receiving a retrieval string.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1 is a perspective side view of a loading unit according to an embodiment of the present disclosure including a shipping cap assembly according to an embodiment of the present disclosure;

FIG. 2 is a perspective of the loading unit and shipping cap assembly shown in FIG. 1, with an introducer member removed;

FIG. 7 is an exploded perspective view of the shipping cap assembly shown in FIG. 1;

FIG. 8 is a perspective end view of the shipping cap assembly shown in FIG. 8;

FIG. 15 is the cross-sectional side view shown in FIG. 14 subsequent to attachment of the shipping cap assembly to the loading unit;

FIG. 16 is an enlarged view of the indicated area of interest shown in FIG. 15;

FIG. 17 is an perspective view of the loading unit and shipping cap assembly shown in FIG. 1 with a shell and a pusher assembly removed;

FIG. 18 is a cross-sectional end view taken along line 18-18 shown in FIG. 17;

FIG. 22 is perspective view of a loading unit according to an alternative embodiment of the present disclosure including a shipping cap assembly according to an alternative embodiment of the present disclosure;

FIG. 23 is a perspective view of the shipping cap assembly shown in FIG. 22;

FIG. 24 is a perspective view of a loading unit according to another embodiment of the present disclosure including a shipping cap assembly according to another embodiment of the present disclosure;

FIG. 25 is a perspective view of the shipping cap assembly shown in FIG. 24.

DETAILED DESCRIPTION

Figure 3:
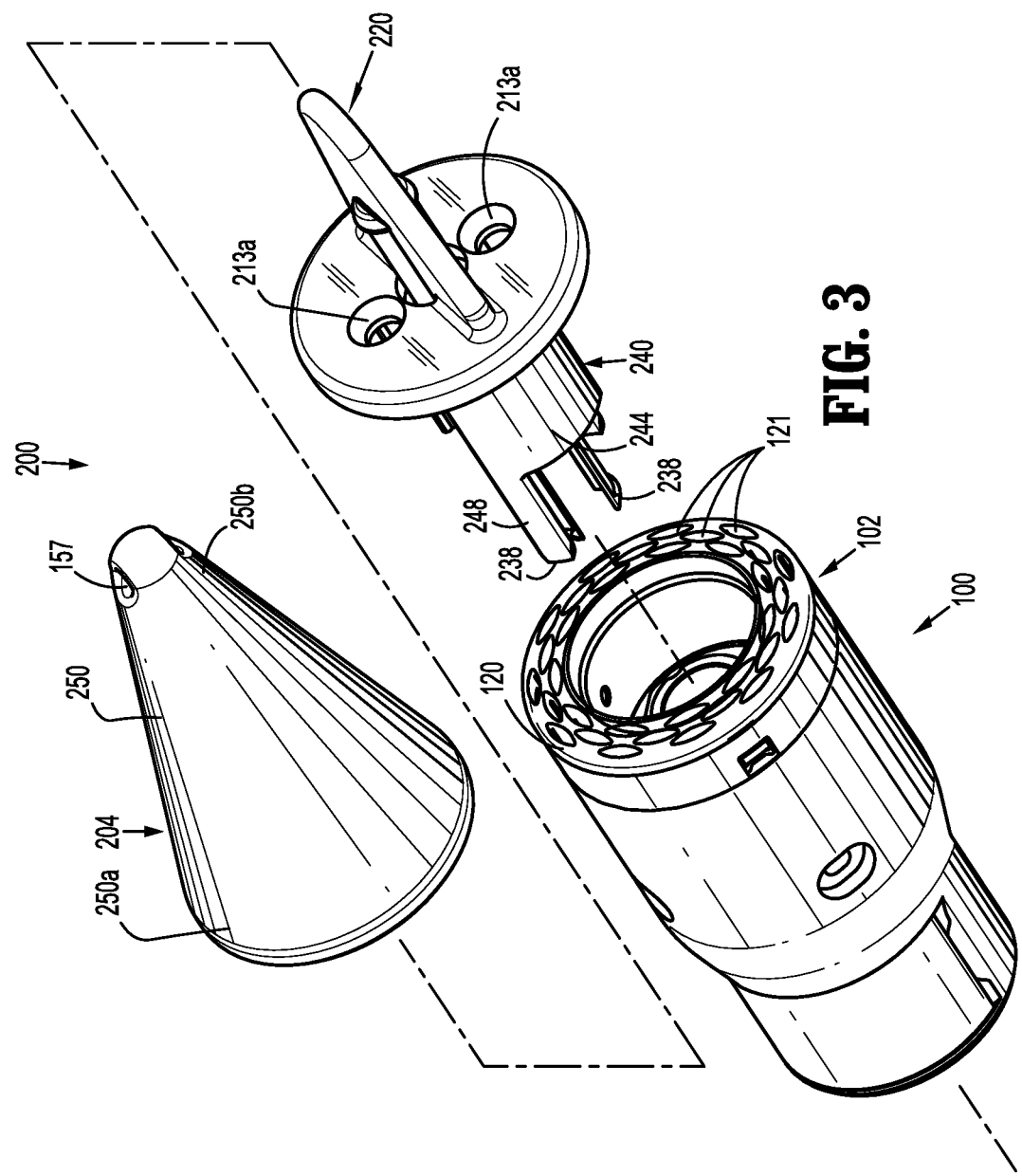
FIG. 3 is a perspective partially exploded view of the loading unit and shipping cap assembly shown in FIG. 1.

Embodiments of the presently disclosed loading unit including a shipping member will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

With reference to FIGS. 1-3, a replaceable loading unit, according to an embodiment of the present disclosure, is shown generally as loading unit 100 and includes a shipping assembly, according to an embodiment of the present disclosure, shown generally as shipping cap assembly 200. Loading unit 100 is configured for operable connection to a surgical stapling device (not shown) and is configured to fire and form an annular array of surgical staples. Shipping cap assembly 200 is selectively received on a distal end 102 of loading unit 100 and operates to maintain staples "S" (FIG. 4) within a staple cartridge 120 of loading unit 100. Shipping cap assembly 200 also operates to prevent premature advancement of a staple pusher assembly 130 (FIG. 4) of loading unit 100 and of a knife assembly 140 (FIG. 4) of loading unit 100 prior to and during attachment of loading unit 100 to an actuation unit (not shown) of a stapling device (not shown) or an adapter assembly (not shown) that is connected to an actuation unit (not shown) of a stapling device (not shown).

Although loading unit 100 will be described with reference to shipping cap assembly 200, and shipping cap assembly 200 will be described with reference to loading unit 100, it is envisioned that the aspects of the present disclosure may be modified for use with loading units and shipping cap assemblies having different configurations. Loading unit 100 will only be described to the extent necessary to fully disclose the aspects of the present disclosure. For a more detailed description of an exemplary loading unit, please refer to commonly owned U.S. Patent Application Publication No. 2013/0181035, the content of which is incorporated by reference herein in its entirety.

Figure 4:
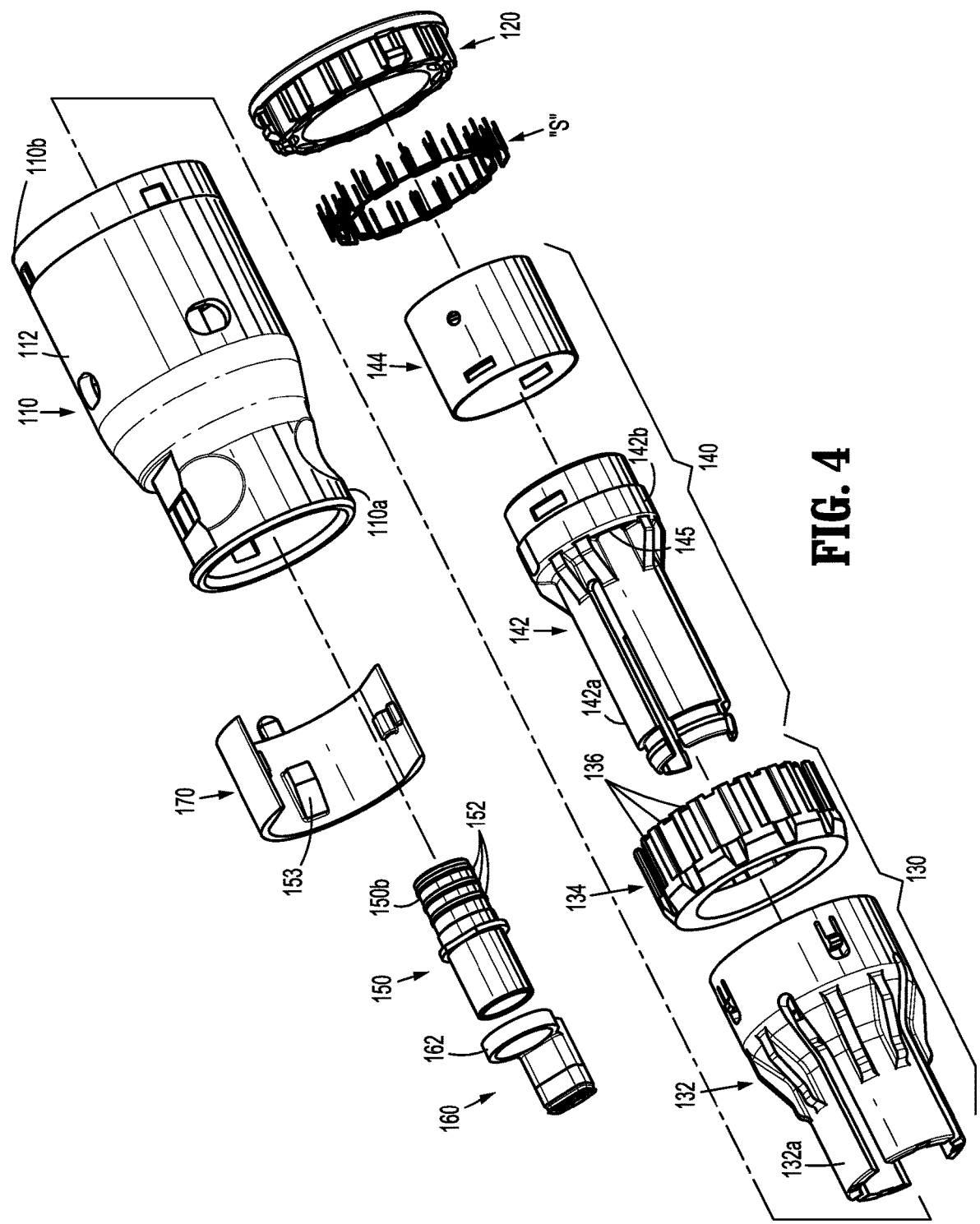
FIG. 4 is a perspective exploded view of the loading unit shown in FIG. 1.
Figure 5:
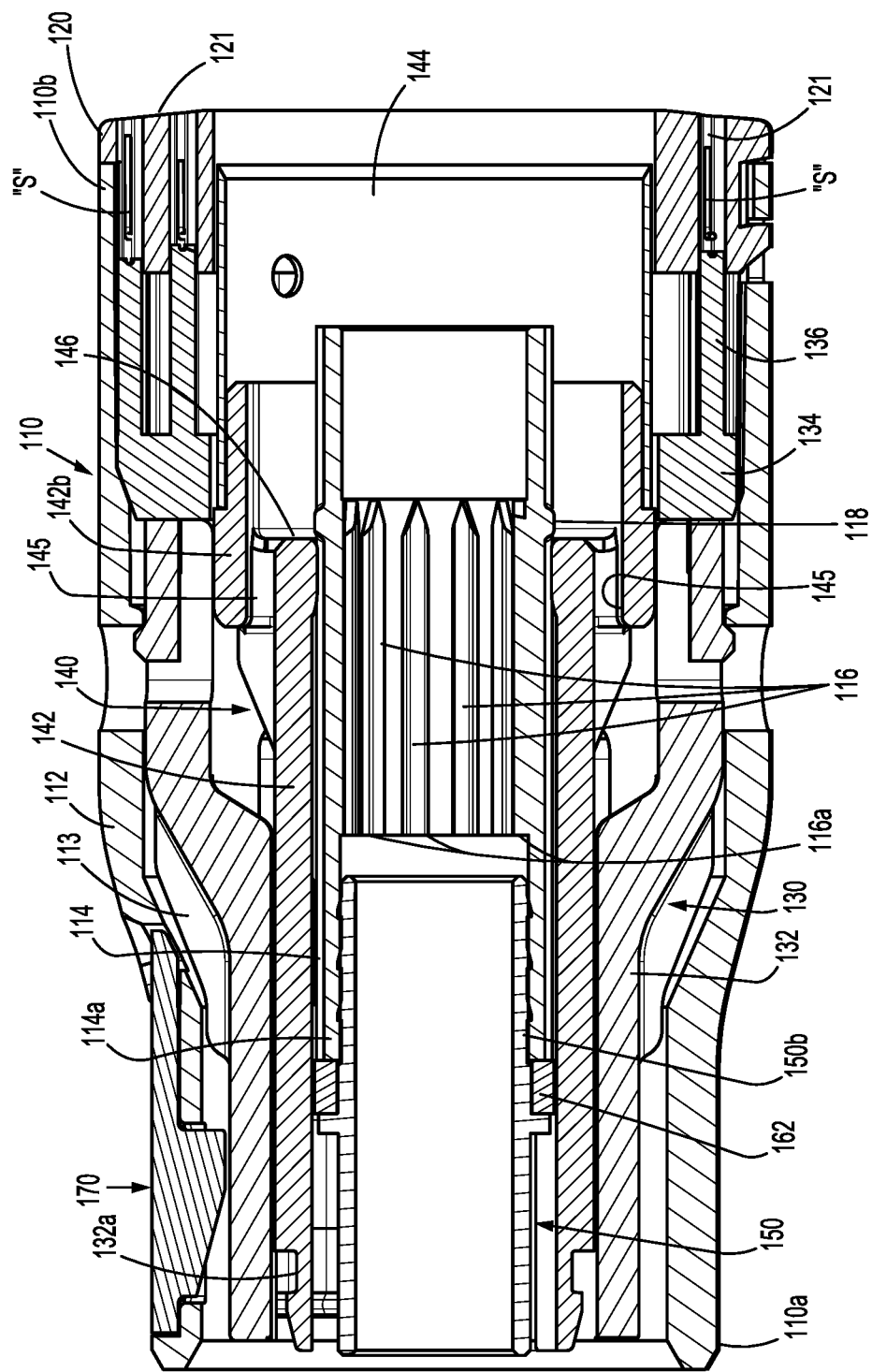
FIG. 5 is a cross-sectional side view of the loading unit shown in FIG. 1.
Figure 6:
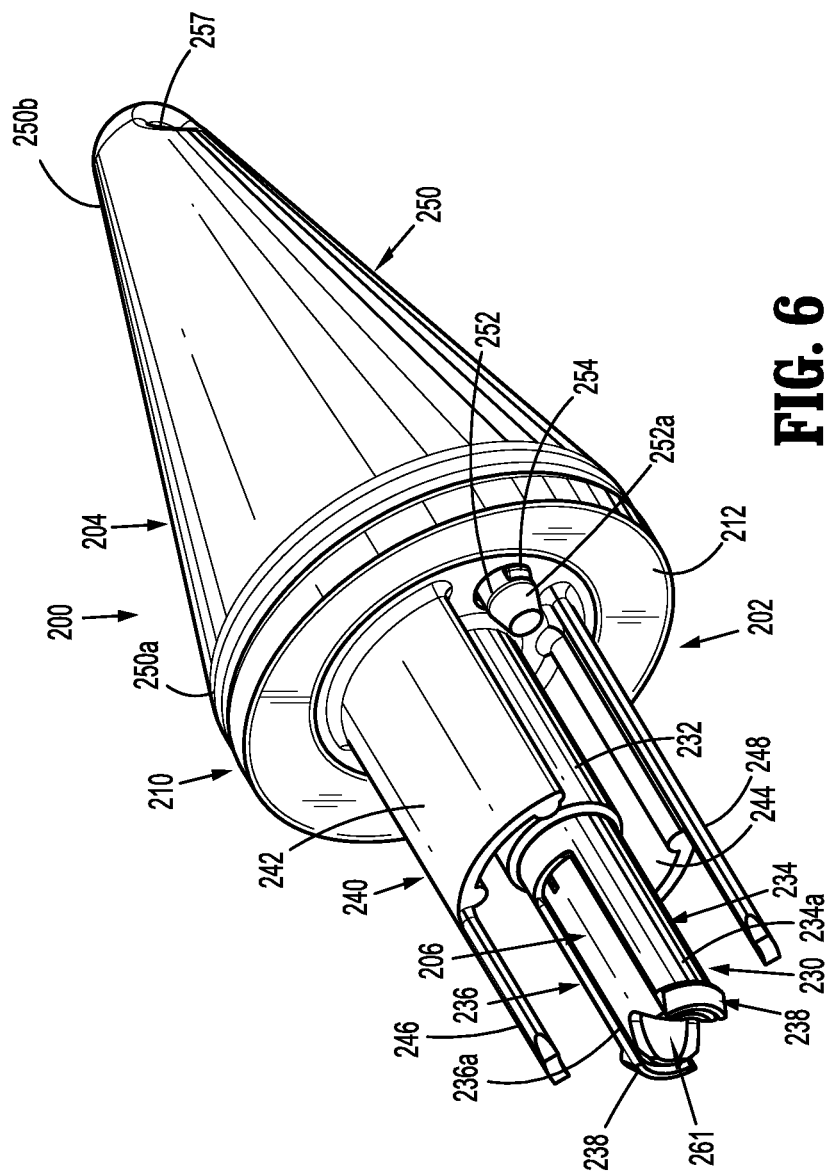
FIG. 6 is a perspective view of the shipping cap assembly shown in FIG. 1.
Figure 9:
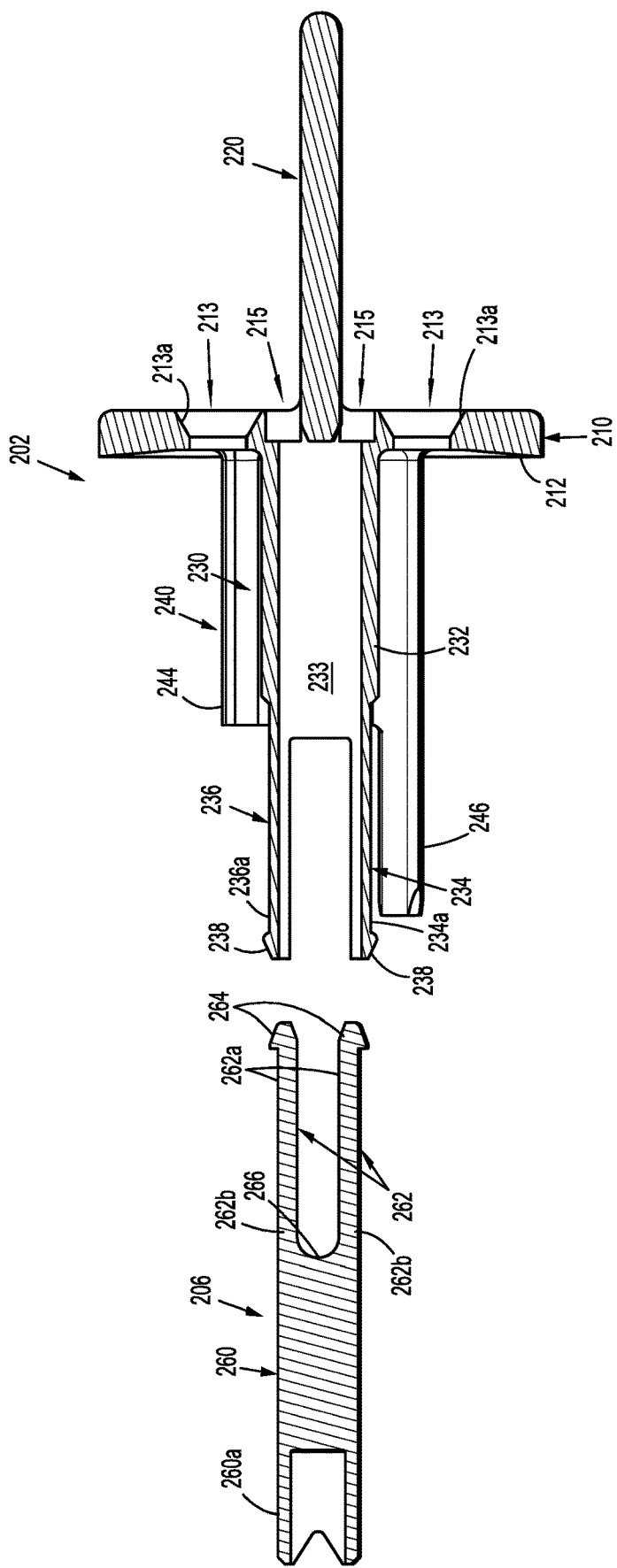
FIG. 9 is a cross-sectional side view taken along line 9-9 shown in FIG. 7.
Figure 10:
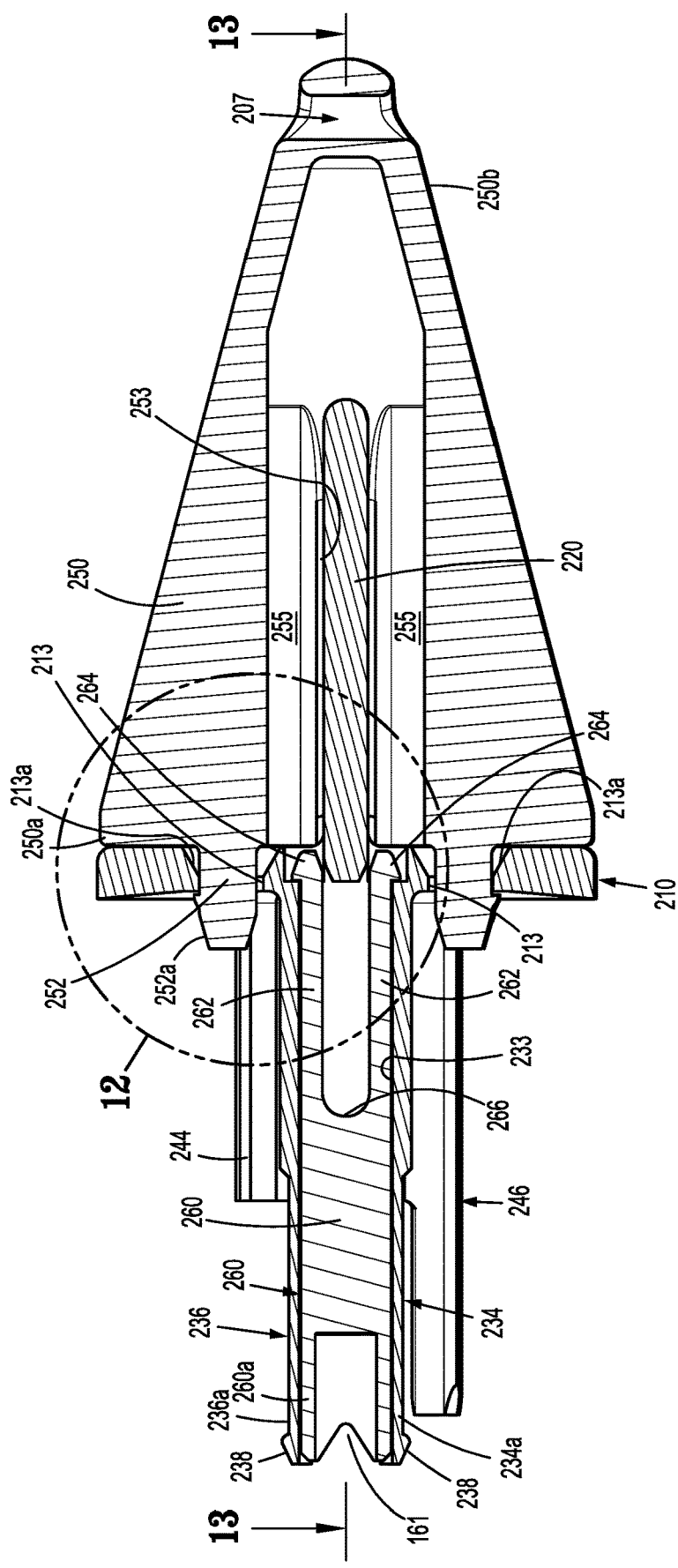
FIG. 10 is a cross-sectional side view taken along line 10-10 shown in FIG. 8.
Figure 11:
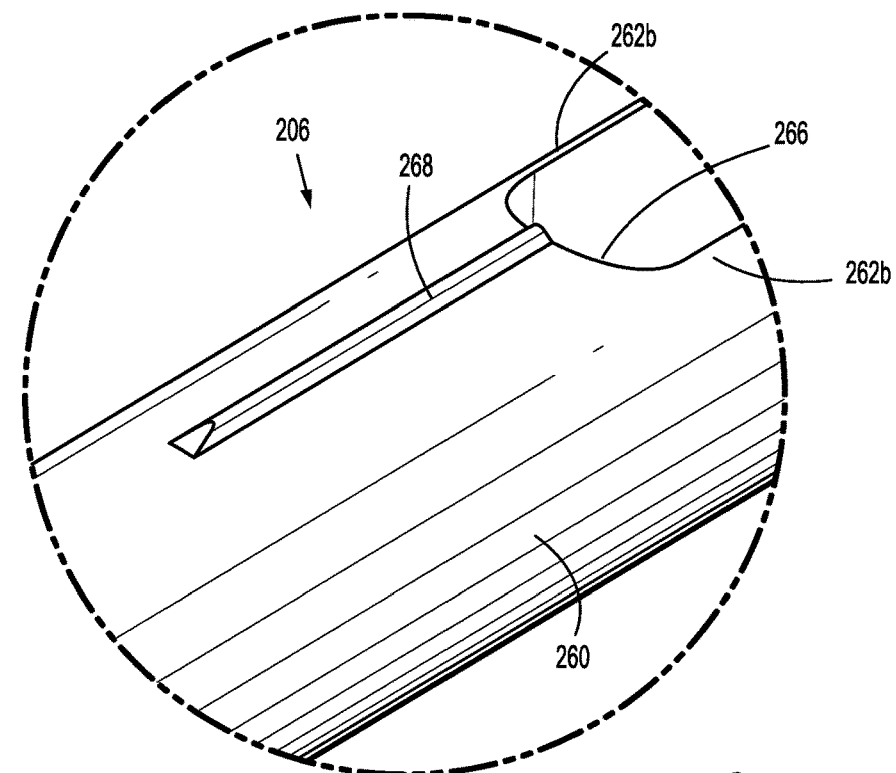
FIG. 11 is an enlarged view of the indicated area of detail shown in FIG. 7.

With reference now to FIGS. 4 and 5, loading unit 100 includes a housing 110, a staple cartridge 120 secured to a distal end 110b of housing 110, a staple pusher assembly 130 operably received within housing 110, a knife assembly 140 operably received within housing 110, a bushing member 150 received within proximal end 110a of housing 110, a chip assembly 160 mounted about bushing member 150, and a cover member 170 selectively securable to a proximal end 110a of housing 110.

Housing 110 of loading unit 100 includes an outer cylindrical portion 112 and an inner cylindrical portion 114. A plurality of ribs (not shown) interconnects outer and inner cylindrical portions 112, 114. Inner cylindrical portion 114 and outer cylindrical portion 112 of housing 110 are coaxial and define a recess 113 (FIG. 5) therebetween configured to operably receive staple pusher assembly 130 and knife assembly 140. Inner cylindrical portion 112 of housing 110 includes a plurality of longitudinal ridges 116 (FIG. 5) extending along an inner surface thereof configured for aligning an anvil assembly (not shown) with loading unit 100 during a stapling procedure. As will be described in further detail below, proximal ends 116a of longitudinal ridges 116 are configured to facilitate selective securement of shipping cap assembly 200 with loading unit 100. An annular ridge 118 (FIG. 5) is formed on an outer surface of inner cylindrical portion 112 and is configured to assist in maintaining knife assembly 140 in a retracted position.

Proximal end 110a of housing 110 is configured for selective connection to an actuation unit (not shown) of a stapling device (not shown) or an adapter assembly (not shown) connected to an actuation unit (not shown) of a stapling device (not shown). Housing 110 of loading unit 100 may be configured for bayonet coupling to the actuation unit and/or the adapter assembly, or for connection to the actuation unit and/or the adapter assembly in any other suitable manner.

Staple cartridge 120 of loading unit 100 is disposed on a distal end 110*b* of housing 110 and includes a plurality of staple pockets 121 configured to selectively retain staples "S". Staple cartridge 120 may be selectively secured to housing 110 to allow replacement of staple cartridge 120 to permit reuse of loading unit 100. Alternatively, staple cartridge 120 is securely affixed to housing 110 allowing for only a single use of loading unit 100.

With continued reference to FIGS. 4 and 5, staple pusher assembly 130 of loading unit 100 includes a pusher adapter 132 and a pusher 134. Although shown as independent components, it is envisioned that pusher adapter 132 and pusher 134 may be integrally formed. A proximal end 132*a* of pusher adapter 132 is configured for operable connection to a drive mechanism (not shown) for advancing pusher adapter 132 and pusher 134 from a first or proximal position (FIG. 5) to a second or distal position (not shown) during actuation of the stapler device (not shown). Pusher 134 includes a plurality of pusher members 136 aligned with staples "S" received within staple pockets 121 of staple cartridge 120. Advancement of pusher 134 relative to staple cartridge 120 causes ejection of the staples from staple cartridge 120.

Still referring to FIGS. 4 and 5, knife assembly 140 of loading unit 100 includes a knife carrier 142 and a circular knife 144 secured about a distal end 142*b* of knife carrier 142. A proximal end 142*a* of knife carrier 142 is configured for operable connection with a drive mechanism (not shown) which moves knife carrier 142 and circular knife 144 from a first or proximal position (FIG. 5) to a second or advanced position (not shown) to cause the cutting of tissue (not shown) disposed adjacent to staple cartridge 120 and within the staple line of staple cartridge 120. Knife carrier 142 defines a pair of openings 145 (FIG. 5). As will be described in further detail below, openings 145 are configured to receive first and second outer legs 246, 248 of outer annular extension 240 of shipping member 202 of shipping cap assembly 200. A ledge 146 (FIG. 5) is disposed adjacent distal end 142*b* of knife carrier 142. As will be described in further detail below, engagement of ledge 146 by ribs 242*a*, 244*a* of first and second shelves 242, 244, respectively, of outer annular extension 240 of shipping member 202 of shipping cap assembly 200 prevents distal advancement of knife assembly 140.

With reference still to FIGS. 4 and 5, an annular flange 162 of chip assembly 160 is received around a distal end 152*b* of bushing member 150. Distal end 152*b* of bushing member 150 is secured within a proximal end 114*a* of inner cylindrical portion 114 of housing 110 by a plurality of ridges 152 formed on distal end 152*b* of bushing member 150. Cover member 170 of loading unit 100 is selectively secured to proximal end 110*a* of housing 110. The cover member 170 is a type of locking collar that enables secure attachment of the reload/loading unit to the adapter. With this cover member/locking collar, no manipulation of the lock is required to attach. A cam surface 153 enables the member 170 to lift up slightly and then snap back. In order to unload, it is necessary to lift the locking collar 170 away from the shell of the reload to disengage the disposable reload from the re-useable adapter (not shown).

Turning now to FIGS. 6-13, shipping cap assembly 200 includes a shipping member 202, an introducer member 204 selectively secured to shipping member 202, and a locking member 206 operably received within shipping member 202. Shipping member 202 includes a base portion 210, a flange portion 220 extending distally from base portion 210, and inner and outer annular extensions 230, 240 extending proximally from base portion 210. Although shown as being of one-piece construction, i.e., integrally or monolithically formed, it is envisioned that any or all of base portion 210, flange portion 220, and inner and outer annular extensions 230, 240 may be independently formed and secured together with adhesive, welding, or in any other suitable manner.

As shown, base portion 210 of shipping member 202 of shipping cap assembly 200 includes a substantially flat or planar body having a circular shape. Although shown having a circular shape, it is envisioned that base portion 210 may include any shape corresponding to the cross-sectional shape of loading unit 100 (FIG. 3). A staple retaining surface 212 of base portion 210 is formed radially outward of outer annular extension 240 and is configured to abut staple cartridge 120 of loading unit 100 when shipping cap assembly 200 is received on distal end 102 (FIG. 3) of loading unit 100 to retain staples "S" within staple pockets 121 (FIG. 3) of staple cartridge 120 during shipment of loading unit 100, during attachment of loading unit 100 to an actuation unit (not shown) of the stapling device (not shown), and during positioning of loading unit 100 within a patient. Although shown as being annular to correspond with the shape of staple cartridge 120, it is envisioned that staple retaining surface 212 may be modified to correspond with staple cartridges of other configurations.

Base portion 210 of shipping member 202 of shipping cap assembly 200 defines a pair of through holes or openings 213 configured to selectively receive protrusions 252 of introducer member 204. Base portion 210 includes a slanted or angled portion 213*a* (FIG. 9) about the pair of openings 213 for facilitating receipt of protrusions 252 therein. Base portion 210 also defines a pair of slots 215 disposed on either side of flange portion 220. As will be described in further detail below, slots 215 are configured to receive leg portions 262 of locking member 206.

Flange portion 220 of shipping member 202 of shipping cap assembly 200 extends distally from base portion 210 and is configured to be selectively received within introducer member 204. Flange portion 220 may also be configured to facilitate engagement of shipping member 202 of shipping cap assembly 200 by a user. As shown, flange portion 220 of shipping member 202 is substantially planar and includes a substantially triangular cross-sectional profile; however, flange portion 220 may include any configuration suitable for receipt within introducer member 204 of shipping cap assembly 200 and/or for facilitating engagement of shipping member 202 by a user. For example, in some embodiments, flange portion 220 includes ridges (not shown) and/or notches (not shown).

With continued reference to FIGS. 6-13, inner annular extension 230 of shipping member 202 of shipping cap assembly 200 is configured to be selectively received within inner cylindrical portion 114 (FIG. 19) of housing 110 of loading unit 100. Inner annular extension 230 includes a cylindrical body 232 and first and second legs 234, 236 extending proximally from cylindrical body 232. Cylindrical body 232 and first and second legs 234, 236 define a longitudinal bore 233 configured for receipt of locking member 206. First and second inner legs 234, 236 each include a free end 234*a*, 236*a*, respectively, configured to flex radially inward towards each other. A projection 238 extends radially outward from each free end 234*a*, 236*a* of respective first and second legs 234, 236. As will be described in further detail below, projections 238 are configured to selectively engage proximal ends 116a (FIG. 5) of ridges 116 formed on the inner surface of inner cylindrical portion 114 of housing 110 of loading unit 100 when shipping assembly 200 is received on distal end 102 of loading unit 100.

Outer annular extension 240 of shipping member 202 of shipping cap assembly 200 is radially spaced from inner annular extension 230 and is configured to be selectively received about inner cylindrical portion 114 of housing 110 of loading unit 100. Inner and outer extensions 230, 240 are coaxial. Outer annular extension 240 includes first and second shelves 242, 244 and first and second outer legs 246, 248. Although first shelf 242 is shown integrally formed with first outer leg 246 and second shelf 244 is shown integrally formed with second outer leg 248, first shelf 242 and first outer leg 246 and second shelf and second outer leg 248 may form separate portions of outer annular extension 240. Further, although outer annular extension 240 is shown having two shelves 242, 244, and two outer legs 246, 248, it is envisioned that outer annular extension 240 may include an annular shelf, a single shelf, or multiple shelves, and may include a single leg or multiple legs.

Each of first and second shelves 242, 244 include ribs 242a, 244a configured to engage ledge 146 (FIG. 20) disposed adjacent distal end 142a of knife carrier 142 of knife assembly 140 of loading unit 100. Although shown as each having a pair of ribs 242a, 244a, it is envisioned that each of first and second shelves 242, 244 may have only a single rib or multiple ribs. It is further envisioned that first and second shelves 242, 244 may instead include a thickened portion along part or all of first and second shelves 242, 244 for engaging ledge 146 of knife carrier 142 of knife assembly 140. Each of first and second outer legs 246, 248 are configured such that free ends 246a, 248a thereof engage pusher adapter 132 of pusher assembly 130 (FIG. 19) of loading unit 100 when shipping cap assembly 200 is received on distal end 102 of loading unit 100.

Figure 12:
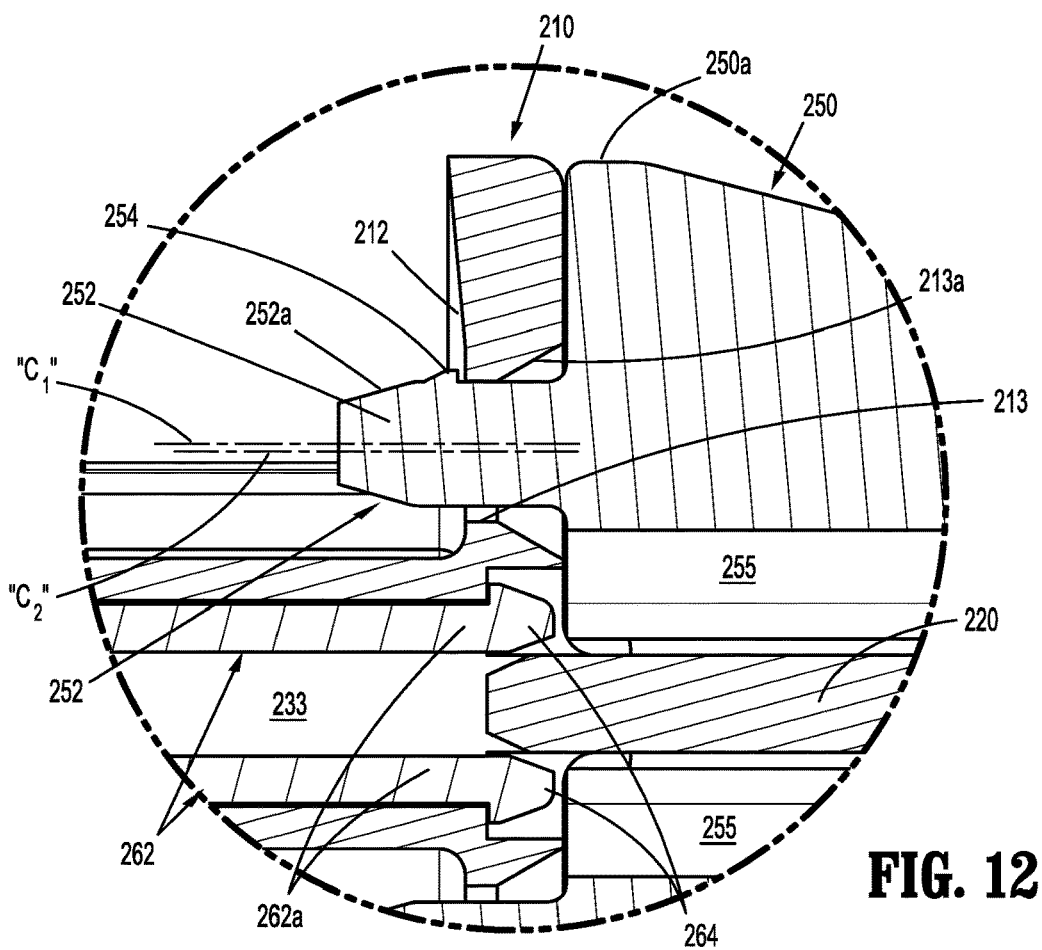
FIG. 12 is an enlarged view of the indicated area of detail shown in FIG. 10.
Figure 13:
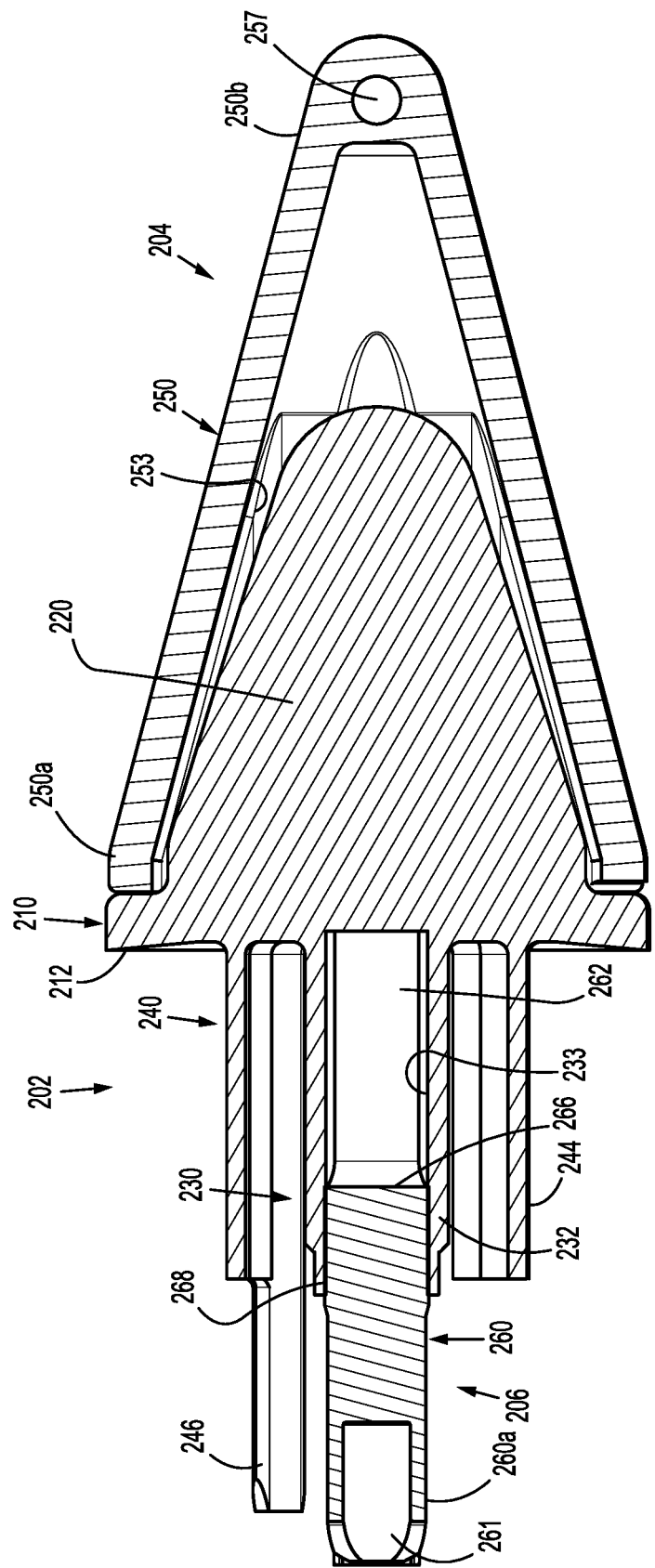
FIG. 13 is a cross-sectional side view taken along line 13-13 shown in FIG. 10.

Still referring to FIGS. 6-13, introducer member 204 of shipping cap assembly 200 includes a substantially conical body 250. Protrusions 252 extend proximally from a proximal end 250a of conical body 250. Proximal ends 252a of protrusions 252 are tapered to facilitate reception of protrusions 252 within openings 213 in base portion 210. Each protrusion 252 includes a tab 254 configured to frictionally engage base portion 210 of shipping member 202 when protrusions 252 are received through openings 213 in base portion 210 to selectively secure introducer member 204 to shipping member 202. Turning briefly to FIG. 12, a centerline "c1" of each protrusion 252 is laterally spaced from a centerline "c2" of each opening 213 in base portion 210 of shipping member 202. In this manner, receipt of protrusion 252 of introducer member 204 within opening 213 in base portion 210 of shipping member 202 biases protrusions 252 radially outward, thereby ensuring engagement of tabs 254 on protrusions 252 with base portion 210. Separation of introducer member 204 from shipping member 202 requires overcoming the biasing force created by the lateral spacing of centerlines "c1", "c2" to allow tabs 254 to disengage from base portion 210 of shipping member 202.

Introducer member 204 of shipping cap assembly 200 defines a longitudinal slot 253 and an annular bore 255 in proximal end 250a of conical body 250. Longitudinal slot 253 is configured to receive flange portion 220 of shipping member 202 when introducer member 204 is engaged with shipping member 202 and annular bore 255 is configured to receive legs 262 of locking member 206 when locking member 206 is in a distal position (FIG. 3). Introducer member 204 further defines a throughbore 257 in a distal end 250b of conical body 250 configured to receive a suture, wire "w" (FIG. 21), cord, or other means for retrieving shipping cap assembly 200 from within a body cavity (not shown) after separation of shipping cap assembly 200 from loading unit 100.

With reference still to FIGS. 6-13, locking member 206 of shipping cap assembly 200 includes a substantially cylindrical body 260 defining a notch 261 in a proximal end 260a and having a pair of legs 262 extending from a distal end 260b. Each leg 262 includes a projection 264 extending radially outward from each free end 262a configured to prevent free ends 262a of legs 262 from retracting through slots 215 in base portion 210 of shipping member 202 once legs 262 have been received within slots 215. An engagement surface 266 is formed between connected ends 262b of legs 262 and is configured to engage base portion 210 of shipping cap 202 when locking member 206 is in the distal position. A longitudinal rib 268 (FIG. 11) extends along an outer surface of cylindrical body 260 and is configured to create friction with an inner surface of cylindrical body 232 of inner annular extension 230 of shipping member 202 to assist in maintaining locking member 206 relative to inner annular extension 230.

Locking member 206 of shipping cap assembly 200 is slidably received within longitudinal bore 233 defined by first and second inner legs 234, 236 and cylindrical body 232 of inner annular extension 230 of shipping member 202. When locking member 206 is received within longitudinal bore 232, free ends 262a of legs 262 of locking member 206 extend through slots 215 in base portion 210. As noted above, projections 264 formed on free ends 262a of legs 262 prevent legs 262 from retracting through slots 215. In a first or unlocked position (FIG. 3), locking member 206 is in the proximal position. In a second or locked position (FIG. 6), locking member 206 is in a distal position in which notch 261 formed in proximal end 260a of cylindrical body 260 is disposed adjacent to free ends 234a, 236a of first and second arms 234, 236 of inner annular extension 230 of shipping member 202.

Figure 14:
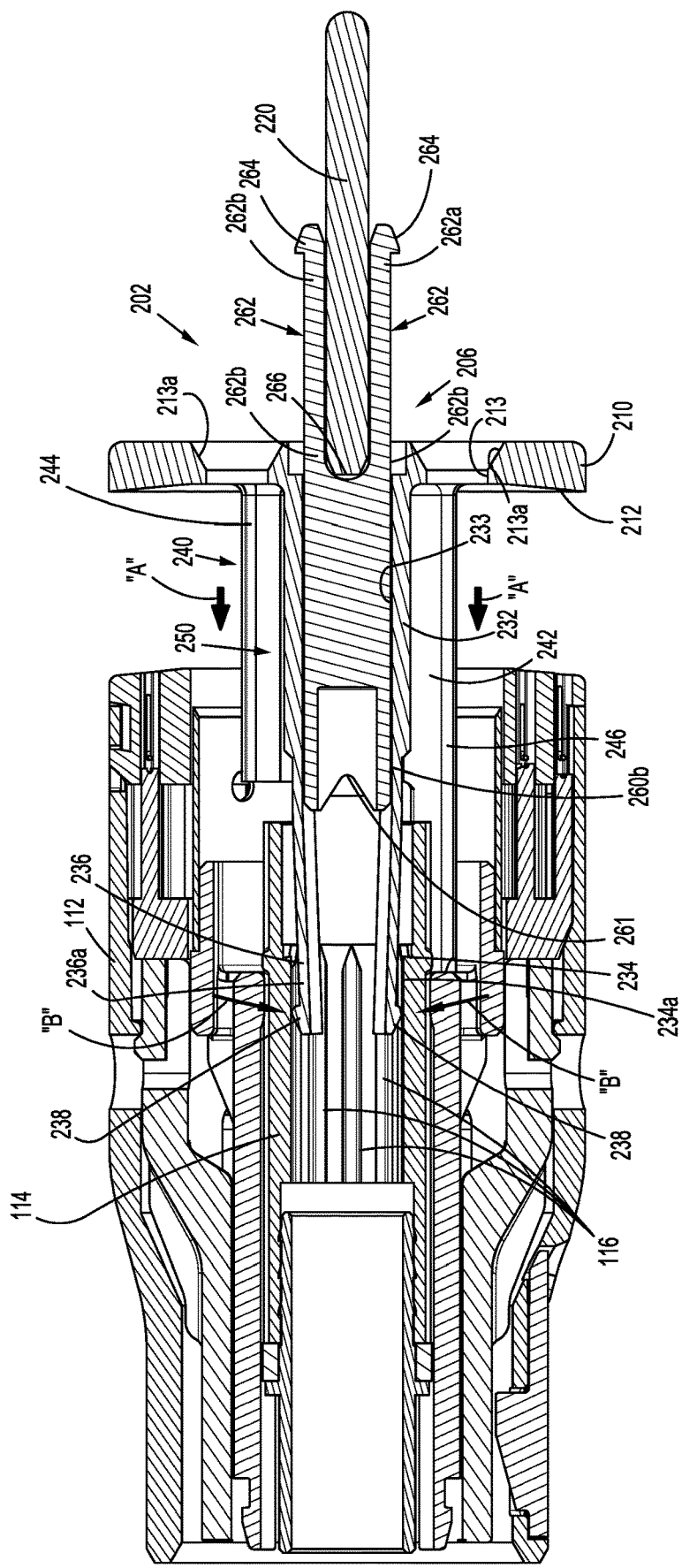
FIG. 14 is a cross-sectional side view of the loading unit and shipping cap assembly shown in FIG. 1 prior to attachment of the shipping cap assembly to the loading unit.

Attachment of shipping cap assembly 200 to loading unit 100 will now be described with reference to FIGS. 14-20. With reference initially to FIG. 14, shipping member 202 and locking member 206 of shipping cap assembly 200 are shown with locking member 206 in the first or unlocked position. In the unlocked position, locking member 206 is in the distal position within longitudinal passage 233 formed by inner annular extension 230 of shipping member 202 and legs 262 of locking member 206 are fully received through slots 215 in base portion 210 of shipping member 202 such that engagement surface 266 of locking member 206 formed between connected ends 262b of legs 262 of locking member 206 engages base portion 210. Prior to attachment of shipping member 202 of shipping cap assembly 200 to loading unit 100 introducer member 204 is separate from shipping member 202.

With reference still to FIG. 14, shipping member 202 and locking member 206 of shipping cap assembly 200 are positioned with loading unit 100 such that first and second inner legs 234, 236 of inner annular extension 230 of shipping member 202 and cylindrical body 260 of locking member 206, which is received within passage 233 of inner annular extension 230, are axially aligned with inner cylindrical portion 114 of housing 110 of loading unit 100. Shipping member 202 is then longitudinally advanced relative to loading unit 100, as indicated by arrows "A", such that first and second inner legs 234, 236 of inner annular extension 230 of shipping member 202 and cylindrical body 260 of locking member 206 are received within inner cylindrical portion 114 of housing 110 of loading unit 100. As first and second inner legs 234, 236 of shipping member 202 are proximally advanced within inner cylindrical portion 114 of loading unit 100, engagement of free ends 234a, 236a of respective first and second legs 234, 236, and more particularly, projections 238 formed on free ends 234a, 236a, with ridges 116 formed within inner cylindrical portion 114 of housing 110 causes free ends 234a, 236a of respective first and second inner legs 234, 236 to flex radially inward towards one another, as indicated by arrows "B".

Turning to FIGS. 15-20, shipping cap assembly 200 is shown attached to loading unit 100. When attached to loading unit 100, staple retaining surface 212 of base portion 210 of shipping member 202 abuts staple cartridge 120 to retain staples "S" within staple pockets 121, first and second shelves 242, 244 (FIG. 20) are received about inner cylindrical portion 114 of housing 110 and first and second outer legs 246, 248 (FIG. 19) of outer annular extension 240 are received through openings 145 formed in knife carrier 142. In addition, free ends 234a, 236a of respective first and second legs 234, 236 extend proximally beyond proximal end 116a of ridges 116 formed within inner cylindrical portion 114 of housing 114. As such, free ends 234a, 236a of respective first and second legs 234, 236 are able to return to an unflexed condition.

With particular reference to FIGS. 15 and 16, when free ends 234a, 236a of respective first and second legs 234, 236 of inner annular extension 230 of shipping member 202 return to the unflexed condition, projections 238 formed on each free end 234a, 236a engage proximal ends 116a of ridges 116 of inner cylindrical portion 114 of housing 110 of loading unit 100. The return of free ends 234a, 236a of respective first and second legs 234, 236 to the unflexed position, as indicated by arrows "C" in FIG. 16, is facilitated by longitudinal movement of cylindrical body 260 of locking member 206 in the proximal direction, as indicated by arrows "D." Locking member 206 is moved in the proximal direction through engagement of free ends 262a of legs 262 of cylindrical body 260. Although it is envisioned that introducer member 206 of shipping cap assembly 200 may be configured to engage free ends 262a of legs 262 as introducer member 206 is secured to shipping member 202, in embodiments, locking member 206 is moved to the proximal position prior to attachment of introducer member 206 to shipping member 202.

Movement of locking member 206 in the proximal direction secures shipping member 202 to loading unit 100. Specifically, engagement of proximal end 260a of cylindrical body 260 of locking member 206 with free ends 234a, 236a of respective first and second legs 234, 236 of inner annular extension 230 ensures that free ends 234a, 236a of respective legs 234, 236 return to the unflexed position, thereby further ensuring that projections 238 formed on each free end 234a, 236a engage proximal ends 116a of ridges 116. Engagement of projections 238 with proximal ends 116a of ridges 116 formed in inner cylindrical portion 114 of housing 110 secures shipping member 202 to loading unit 100.

As long as proximal end 260a of cylindrical body 260 of locking member 206 remains positioned between free ends 234a, 236a of respective legs 234, 236, free ends 234a, 236a of respective first and second legs 234, 236 are prevented from flexing radially inward. Because free ends 234a, 236a of legs 234, 236 are prevented from flexing inward, projections 238 formed on free ends 234a, 236a remain in contact with proximal ends 116a of ridges 116, thereby ensuring that shipping member 202 remains secured to loading unit 100. Projections 264 formed on free ends 262a of legs 262 of cylindrical body 260 of locking member 206 engage base portion 210 of shipping member 202 to maintain cylindrical body 260 of locking member 206 relative to shipping member 202.

Figure 19:
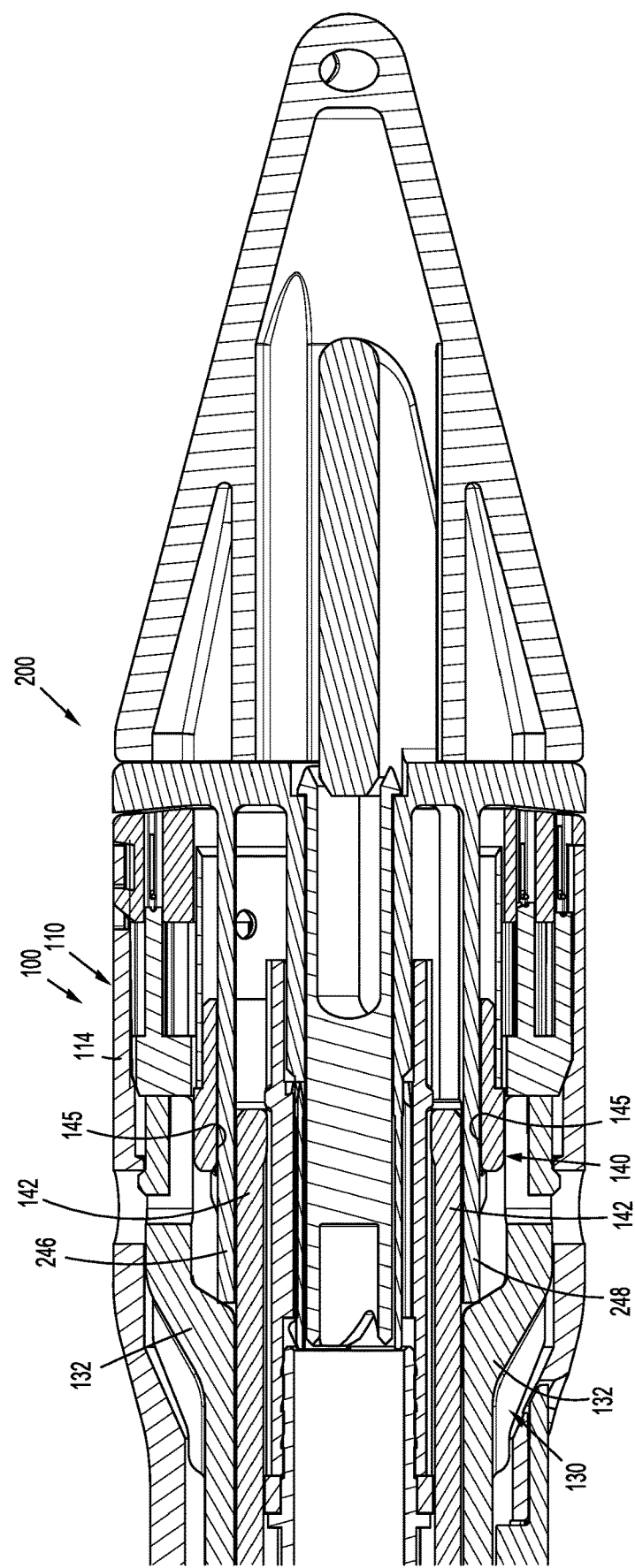
FIG. 19 is a cross-sectional side view taken along line 19-19 shown in FIG. 18.

With particular reference to FIG. 17, as noted above, when shipping member 202 of shipping cap assembly 200 is attached to loading unit 100, first and second outer legs 246, 248 of outer annular extension 240 of shipping member 202 of shipping cap assembly 200 are received through openings 145 formed in knife carrier 142 of knife assembly 140 of loading unit 100. Turning to FIG. 19, when received through openings 145 of knife carrier 142, each of outer legs 246, 248 engage pusher member 132 of pusher assembly 130. Engagement of pusher member 132 by outer legs 246, 248 prevents longitudinal movement of pusher member 132 as long as shipping member 202 is secured to loading unit 100.

Figure 20:
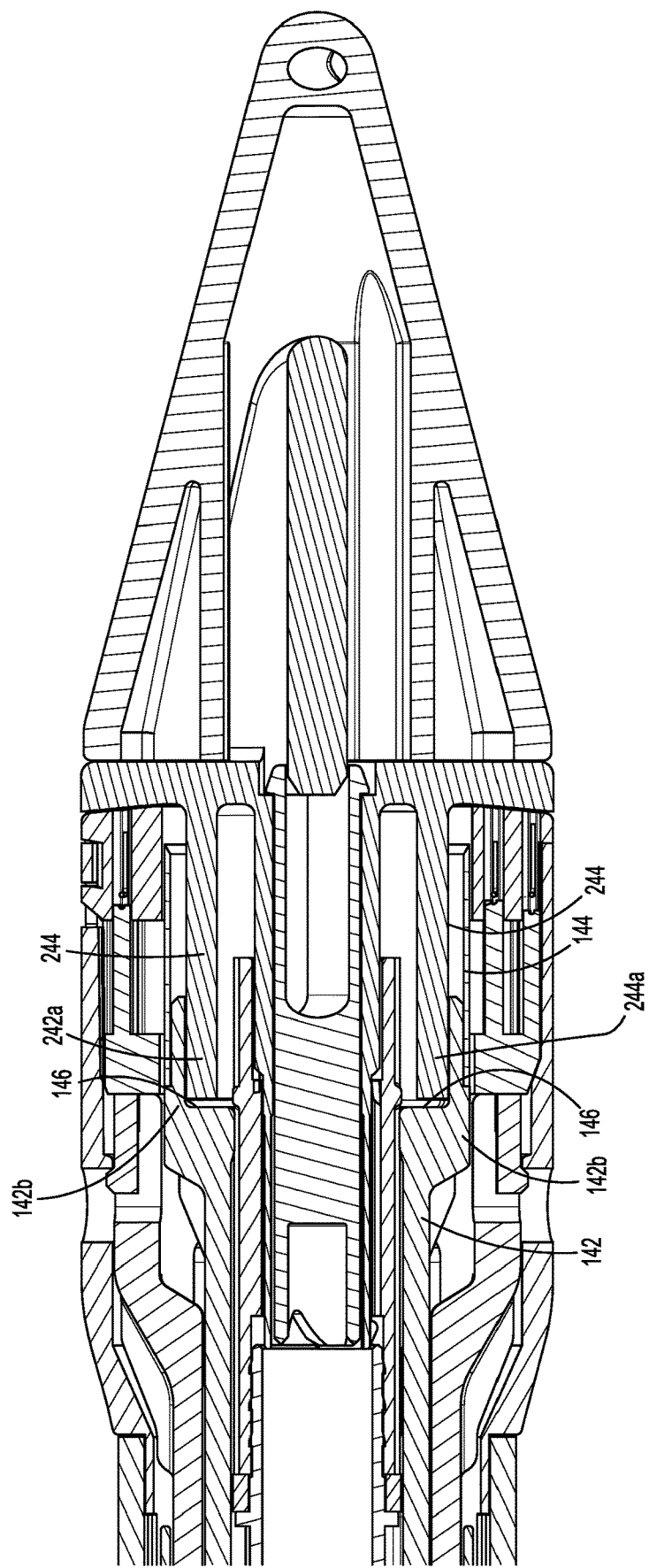
FIG. 20 is a cross-sectional side view taken along line 20-20 shown in FIG. 18.

With reference now to FIG. 20, as noted above, when shipping member 202 of shipping cap assembly 200 is attached to loading unit 100, first and second shelves 242, 244 are received about inner cylindrical portion 114 of housing 110. Ribs 242a, 244a formed on respective first and second shelves 242, 244 engage ledge 146 disposed adjacent distal end 142b of knife carrier 142 of knife assembly 140 of loading unit 100. Engagement of knife carrier 142 by ribs 242a, 244a of first and second shelves 242, 244 prevents longitudinal movement of knife carrier 142 as long as shipping member 202 is secured to loading unit 100.

Once shipping member 202 of shipping cap assembly 200 is secured to loading unit 100, introducer member 204 may be secured to shipping member 202. Alternatively, loading unit 100 may be used without introducer member 204. Introducer member 206 is secured to shipping member 202 in the manner described above. In particular, introducer member 204 is positioned relative to shipping member 202 such that flange 220 of shipping member 202 is aligned with longitudinal slot 253 formed in body 250 of introducer member 204. Introducer member 204 is then longitudinally advanced relative to shipping member 202 such that flange 220 is received within longitudinal slot 253. As introducer member 204 is advanced relative to shipping member 202, protrusions 252 extending from proximal end 250a of conical body 250 of introducer member 204 are received within openings 213 formed in base 210 of shipping member 202. Sloped portions 213a of base 210 and tapered proximal ends 252a of protrusions 252 facilitate reception of protrusion 252 within openings 213. Tabs 254 formed on each protrusion 252 and the offset positioning of centerlines "c1", "c2" (FIG. 12) of protrusions 252 and opening 213 ensure that introducer member 204 remains secured to shipping member 202.

Figure 26:
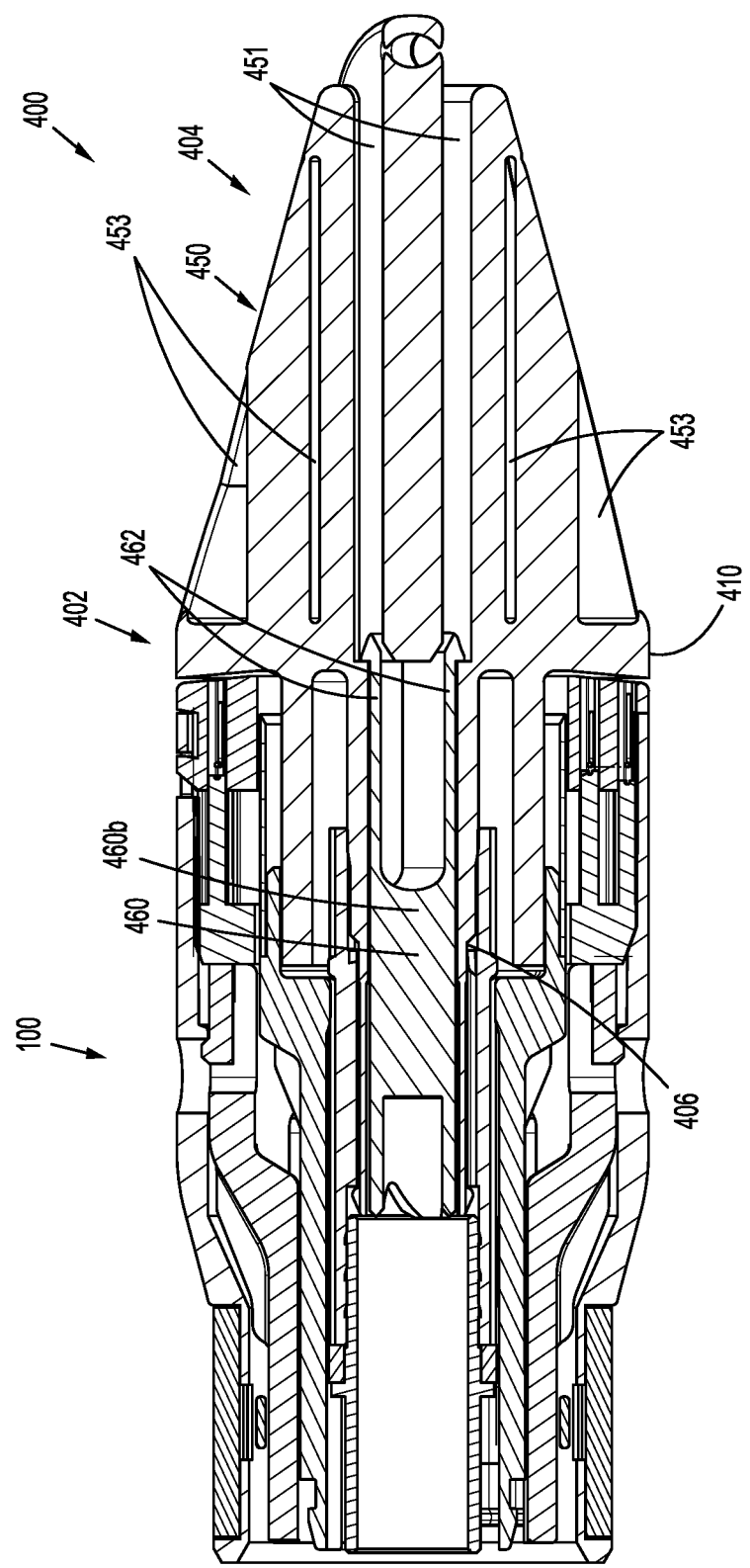
FIG. 26 is a cross-sectional side view of the loading unit and the shipping cap assembly shown in FIG. 24.

It is envisioned that loading unit 100 is provided to a clinician with shipping cap assembly 200 previously attached, however, shipping cap assembly 200 may be provided to a clinician separate from loading unit 100. As noted above, introducer member 204 of shipping cap assembly 200 may be attached to shipping member 202 or may require attachment to shipping member 202. It is envisioned that shipping cap assembly 200 may be provided as a kit with one or more introducer members having alternative configurations (see, for example, FIG. 24). It is also envisioned that shipping cap assembly may be provided without an introducer member (FIG. 26).

Loading unit 100 may be secured to an actuation unit (not shown) of a stapling device (not shown) or an adapter assembly (not shown) connected to an actuation unit (not shown) of a stapling device (not shown) in any traditional manner. As discussed above, in one embodiment, loading unit 100 is secured to an adapter assembly with a bayonet coupling. Once attached to the actuation unit, loading unit 100 positioned within a body cavity of a patient in a traditional manner. Positioning of loading unit 100 may be through an incision or an access port, or in any other manner. Introducer member 204 of shipping cap assembly 200 facilitates positioning of loading unit 100. A wire "w" (FIG. 21), cord, suture, or other means of retrieving shipping cap assembly 200 may be secured to shipping cap assembly 200 using throughbore 257 formed on distal end 250b of conical body 250 of introducer member 204 prior to positioning of loading unit 100.

It is noted that the shipping cap assembly has a shipping member 202 with a flange 220. The flange 220 has a tapered shape that corresponds to an interior space within the introducer member 204 conical body 250. A slot 253 can be provided for receiving the flange 220 and connecting the shipping member to the introducer member. Furthermore, the shipping member has a movable locking member 206 secures the shipping member to the loading unit 100. For example, the locking member 206 can be movable in a proximal direction to lock the position of the shipping member onto the loading unit. In any of the embodiments disclosed herein, a kit having the loading unit, introducer member, and shipping member pre-attached is contemplated. The loading units can be provided in different sizes; more specifically, staple lines having different diameters. The introducer member and shipping member may be provided pre-attached for sizes frequently used in bariatric surgical procedures and not provided in loading units of different sizes, such as those frequently used for colorectal surgical procedures. Another potential benefit of the shipping member is loading safety. Aggressive manipulation of reloads can result in premature movement of the staples and/or knife, but the shipping member enables ergonomic placement of a user's hand over the top of the reload/loading unit with no danger of the staples or knife being contacted by the user.

Figure 21:
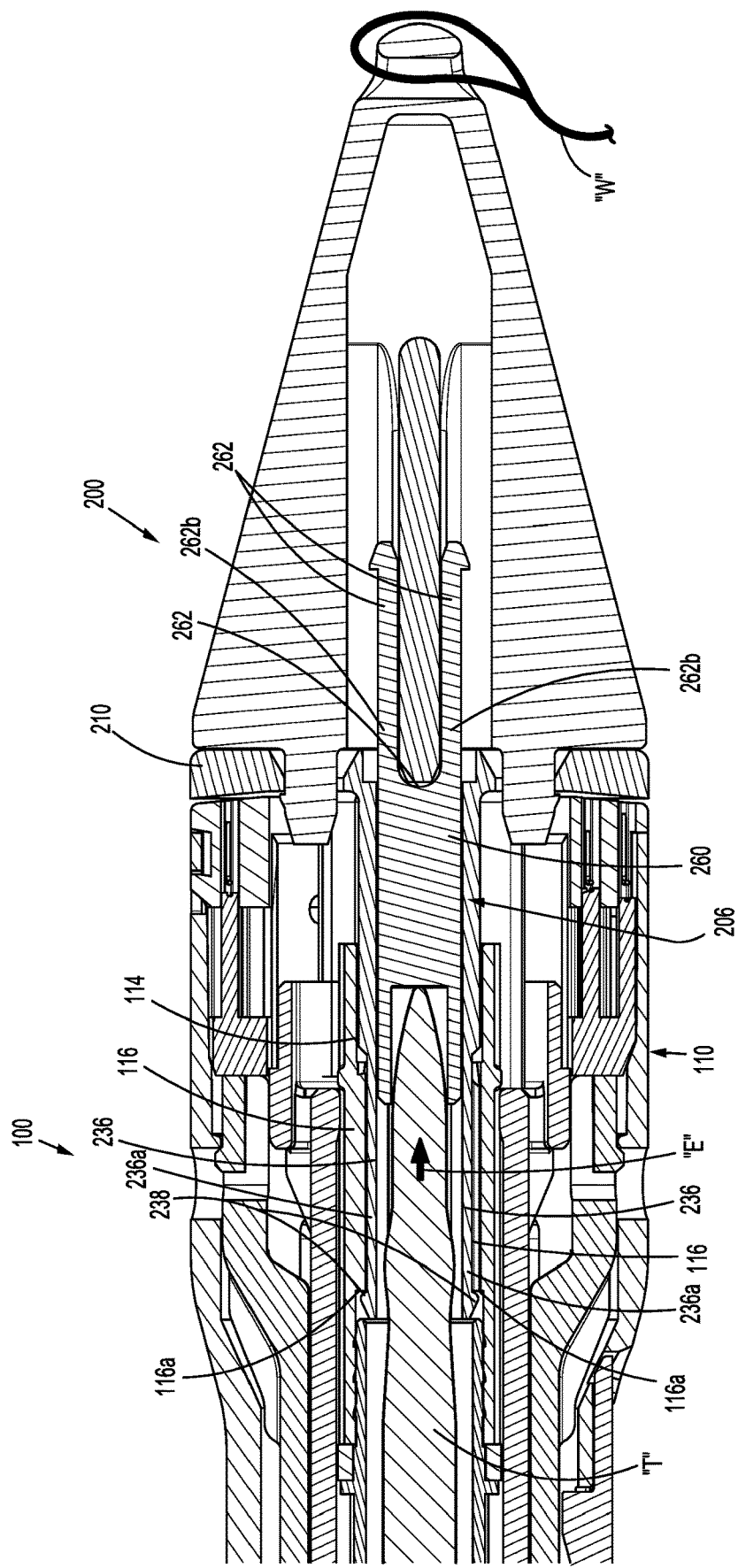
FIG. 21 is the cross-sectional side view shown in FIG. 14 prior to separation of the shipping cap assembly from the loading unit.

With reference now to FIG. 21, once positioned within the body cavity of a patient, shipping cap assembly 200 is separated from loading unit 100 before an anvil assembly (not shown) can be attached to loading unit 100 and tissue (not shown) can be stapled. Separation of shipping cap assembly 200 from loading unit 100 is achieved through distal advancement of a trocar "T", as indicated by arrow "E," into engagement with proximal end 260 of locking member 206. Continued distal advancement of trocar "T" causes movement of locking member 206 to the distal position. When locking member 206 is in the distal position, proximal end 260a of cylindrical body 260 of locking member 206 is no longer positioned between free ends 234a, 236a of respective first and second legs 234, 236 of inner annular extension 230 of shipping member 202. As such, free ends 234a, 236a of respective first and second legs 234, 236 are able to flex radially inward.

Once notch 266 formed between connected ends 262b of cylindrical body 260 of locking member 206 engages base 210 of shipping member 202, continued distal movement of trocar "T" relative to loading unit 100 exerts a force against shipping member 202 of shipping cap assembly 200. Since free ends 234a, 236a of respective first and second legs 234, 236 are no longer prevented from flexing radially inward, the force exerted on shipping member 202 through distal movement of trocar "T" causes free ends 234a, 236a of respective first and second legs 234, 236 to flex radially inward. Flexion of free ends 234a, 236a of respective first and second legs causes projections 238 formed on each of free ends 234a, 236a to disengage from proximal ends 116a of ridges 116 formed on inner cylindrical portion 114 of housing 110 of loading unit 100. In this manner, shipping member 202 of shipping cap assembly 200 is no longer secured to loading unit 100. Continued distal movement of trocar "T" causes shipping member 202 to separate from loading unit 100.

Upon complete separation of shipping member 202 of shipping cap assembly 200 from loading unit 100, loading unit 100 may be used in a traditional manner to staple tissue. Shipping cap assembly 200 may be retrieved from within the body cavity (not shown) using wire "w" or in any other suitable manner.

The introducer member is used, in conjunction with the shipping cap, to aid in the insertion of the device into the body cavity. Once the instrument head is in the operating space, the introducer member and shipping member can be ejected from the device, as discussed above. The introducer member and shipping member are retained by a suture for removal.

With reference to FIGS. 22 and 23, an alternative embodiment of a shipping assembly according to the present disclosure is shown generally as shipping cap assembly 300. Shipping cap assembly 300 is substantially similar to shipping cap assembly 200 described hereinabove, however, shipping cap assembly 300 does not include an introducer assembly. In this manner, base portion 310 of shipping member 302 of shipping cap assembly 300 does not include openings for receiving protrusions of an introducer assembly. Shipping cap assembly 300 is attached to and separated from loading unit 100 in the same manner as shipping cap assembly 200 is attached to and separated from loading unit 100.

With reference now to FIGS. 24-26, another embodiment of a shipping assembly according to the present disclosure is shown generally as shipping cap assembly 400. Shipping cap assembly 400 is substantially similar to shipping cap assembly 200 and will only be described as relates to the differences therebetween. Unlike shipping cap assembly 200 which includes a shipping member 202 (FIG. 3) and a separate introducer member 204 (FIG. 3), a shipping member 402 of shipping cap assembly 400 includes an introducer portion 404 integrally formed with base portion 410. Although shown as being integrally formed with base portion 410 of shipping member 402, it is envisioned that introducer portion 404 may be fixedly secured to base portion 410 using adhesives, mechanical fasteners, or in any other suitable manner.

With continued reference to FIGS. 24-26, introducer portion 404 of shipping member 402 defines a substantially conical body 450 defining a pair of longitudinal slots 451 extending therethrough and a plurality of cutouts 453 formed along an outer surface thereof. Longitudinal slots 451 are configured to receive legs 462 formed on a distal end 460b of a cylindrical body 460 of a locking member 406. Longitudinal slots 451 extend completely through conical body 450 of introducer portion 404 to permit access to legs 462 in order to move locking member 406 from a distal position (not shown) to the proximal position (FIG. 26) during attachment of shipping cap assembly 400 to loading unit 100. Cutouts 453 in conical body 450 of introducer assembly 404 may be configured to facilitate operable engagement by a user. Alternatively, and/or in addition, cutouts 453 may be configured to facilitate insertion of loading unit 100 into a body cavity (not shown).

Shipping cap assembly 400 is attached to loading unit 100 in substantially the same manner as shipping cap assembly 200 is attached to loading unit 100, however, as noted above, introducer portion 450 is integrally formed with base portion 410 of shipping member 402, therefore, introducer portion 450 does not have to be secured to base portion 410 independently. Further, access to legs 462 of cylindrical body 460 of locking member 406 to move locking member 406 from the distal position (not shown) to the proximal position (FIG. 26) to secure shipping member 402 to loading unit 100 is through longitudinal slots 451 formed in conical body 450 of introducer portion 404.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A shipping assembly for a surgical loading unit of a surgical stapler, the shipping assembly comprising:
    a shipping member including a base portion, an inner annular extension extending from the base portion, and an outer annular extension extending from the base portion;
    an introducer member selectively secured to the base portion of the shipping member, the introducer member defining a throughbore configured to receive a retrieval member; and
    a locking member slidably disposed within the inner annular extension and being movable between a proximal position wherein the shipping member is secured to a surgical loading unit and a distal position wherein the shipping member is separable from the surgical loading unit.

2. The shipping assembly of claim 1, further including at least one shelf configured to engage a knife assembly of the surgical loading unit to prevent movement of the knife assembly.

3. The shipping assembly of claim 2, wherein the at least one shelf is formed on the outer annular extension.

4. The shipping assembly of claim 1, further including at least one outer leg configured to engage a pusher assembly of the surgical loading unit to prevent movement of the pusher assembly.

5. The shipping assembly of claim 4, wherein the at least one outer leg extends from the outer annular extension.

6. The shipping assembly of claim 1, wherein the base portion includes a staple retaining surface positionable adjacent a cartridge assembly of the surgical loading unit.

7. The shipping assembly of claim 1, wherein the inner annular extension includes a pair of legs each configured to selectively engage a housing of the surgical loading unit for securing the shipping assembly to the surgical loading unit.

8. The shipping assembly of claim 1, further including a flange portion extending from the base portion, the flange portion being configured for operable engagement by a user.

9. The shipping assembly of claim 8, wherein the introducer member is selectively securable to the flange portion.

10. The shipping assembly of claim 9, wherein the introducer member includes a conical shape.

11. The shipping assembly of claim 9, wherein the introducer member is configured to facilitate insertion of the surgical loading unit through a lumen.

12. The shipping assembly of claim 9, wherein the introducer member is secured to the base portion by a friction fit.

13. The shipping assembly of claim 1, wherein the locking member is configured to be engaged by a trocar member of a surgical stapler.

14. The shipping assembly of claim 1, wherein the retrieval member includes a suture, a wire, a cord, or a string.

15. The shipping assembly of claim 1, wherein the locking member is configured to be engaged by a trocar member of a surgical stapler.

16. A shipping assembly for a surgical loading unit of a surgical stapler, the shipping assembly comprising:
    a shipping member including a base portion, an inner annular extension extending from the base portion, and an outer annular extension extending from the base portion;
    an introducer member selectively secured to the base portion of the shipping member; and
    a locking member slidably disposed within the inner annular extension and being movable relative to the shipping member between a proximal position wherein the shipping member is secured to a surgical loading unit and a distal position wherein the shipping member is separable from the surgical loading unit.

17. The shipping assembly of claim 16, wherein the shipping assembly is secured to the surgical loading unit when the locking member is in the proximal position and the shipping assembly is separable from the surgical loading unit when the locking member is in the distal position.

18. The shipping assembly of claim 16, further including at least one outer leg configured to engage a pusher assembly of the surgical loading unit to prevent movement of the pusher assembly.

19. The shipping assembly of claim 16, wherein the introducer member defines a throughbore configured to receive a retrieval suture.

* * * * *